US012778996B2

(12) United States Patent
Klein et al.

(10) Patent No.: US 12,778,996 B2
(45) **Date of Patent: *Nov. 3, 2026**

(54) COMPOSITIONS AND METHODS FOR TREATING ALZHEIMER'S DISEASE

(71) Applicants: Northwestern University, Evanston, IL (US); Consejo Nacional de Investigaciones Científicas y Técnicas, Buenos Aires (AR); Universidade Federal do Rio de Janeiro, Rio de Janeiro (BR)

(72) Inventors: William L. Klein, Winnetka, IL (US); Diana Jerusalinsky, Buenos Aires (AR); Sergio T. Ferreira, Rio de Janeiro (BR); Maria Clara Selles, Rio de Janeiro (BR); Adriano S. Sebollela, Rio de Janeiro (BR)

(73) Assignees: Northwestern University, Evanston, IL (US); Universidade Federal do Rio de Janeiro, Buenos Aires (AR); Consejo Nacional de Investigaciones Científicas y Técnicas, Rio de Janeiro (BR)

( * ) Notice: Subject to any disclaimer, the term of this patent is extended or adjusted under 35 U.S.C. 154(b) by 677 days.

This patent is subject to a terminal disclaimer.

(21) Appl. No.: 18/149,546

(22) Filed: Jan. 3, 2023

(65) Prior Publication Data

US 2024/0238355 A1 Jul. 18, 2024

Related U.S. Application Data

(63) Continuation of application No. 16/820,269, filed on Mar. 16, 2020, now Pat. No. 11,541,086.

(60) Provisional application No. 62/818,483, filed on Mar. 14, 2019.

(51) Int. Cl.

*A61K 35/76* (2015.01)
*A61K 9/00* (2006.01)
*C07K 16/18* (2006.01)

(52) U.S. Cl.

CPC ............ *A61K 35/76* (2013.01); *A61K 9/0085* (2013.01); *C07K 16/18* (2013.01); *C07K 2317/622* (2013.01)

(58) Field of Classification Search

CPC .................. A61K 35/76; A61K 9/0085; A61K 2039/505; C07K 16/18; C07K 2317/622; C07K 2317/70; A61P 25/28; C12N 2750/14143

See application file for complete search history.

(56) References Cited

U.S. PATENT DOCUMENTS

| | | | |
|---|---|---|---|
| 4,816,567 A | 3/1989 | Cabilly et al. | |
| 4,828,981 A | 5/1989 | Maggio | |
| 4,946,778 A | 8/1990 | Ladner et al. | |
| 5,260,203 A | 11/1993 | Ladner et al. | |
| 8,568,992 B2 | 10/2013 | Walker et al. | |
| 2018/0339065 A1* | 11/2018 | Wilson .................... | A61P 31/12 |

FOREIGN PATENT DOCUMENTS

| | | |
|---|---|---|
| WO | WO88/01649 | 3/1988 |

OTHER PUBLICATIONS

Kussie et al. "A single engineered amino acid substitution changes antibody fine specificity." Journal of immunology (Baltimore, Md.: 1950) 152.1 (1994): 146-152 (Year: 1994).*

Chen et al. "Enhancement and destruction of antibody function by somatic mutation: unequal occurrence is controlled by V gene combinatorial associations." The EMBO journal 14.12 (1995): 2784-2794 (Year: 1995).*

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Ausubel et al., Current Protocols in Molecular Biology, Greene Publishing Associates and John Wiley & Sons, New York, N.Y. 1994.

Beigert et al., Sequence context-specific profiles for homology searching. Proc Natl Acad Sci U S A. Mar. 10, 2009;106(10):3770-5.

Boster. How To Determine Antibody Cross-Reactivity accessed from bosterbio.com on Apr. 22, 2022.

Braitbard et al., Competition between bound and free peptides in an ELISA-based procedure that assays peptides derived from protein digests. Proteome Sci. May 31, 2006;4:12.

Chabrier et al., Synergistic effects of amyloid-beta and wild-type human tau on dendritic spine loss in a floxed double transgenic model of Alzheimer's disease. Neurobiol Dis. Apr. 2014;64:107-17.

Chen et al. Enhancement and destruction of antibody function by somatic mutation: unequal occurrence is controlled byV gene combinatorial associations. EMBO 1995, 14(12):2784-2794.

Chothia et al., Canonical structures for the hypervariable regions of immunoglobulins. J Mol Biol. Aug. 20, 1987;196(4):901-17.

Chothia et al., Conformations of immunoglobulin hypervariable regions. Nature. Dec. 21-28, 1989;342(6252): 877-83.

Chromy et al., Self-assembly of Abeta(1-42) into globular neurotoxins. Biochemistry. Nov. 11, 2003;42(44):12749-60.

(Continued)

*Primary Examiner* — Fereydoun G Sajjadi
*Assistant Examiner* — Alexander W Nicol
(74) *Attorney, Agent, or Firm* — David W. Staple; Casimir Jones, S.C.

(57) ABSTRACT

Provided herein are antibodies against amyloid-beta (Aβ) oligomers, and methods of use thereof for the treatment of Alzheimer's disease (AD). In particular, neauronal expression of single-chain variable fragment (scFv) antibodies against Aβ oligomers is provided as a therapeutic approach in the treatment of AD.

4 Claims, 9 Drawing Sheets

Specification includes a Sequence Listing.

(56) References Cited

OTHER PUBLICATIONS

Clackson et al. Making antibody fragments using phage display libraries. Nature. Aug. 15, 1991;352(6336):624-8.
Cuchet et al., Characterization of antiproliferative and cytotoxic properties of the HSV-1 immediate-early ICPo protein. J Gene Med. Sep. 2005;7(9):1187-99.
Cummings et al., , Alzheimer's disease drug development pipeline: 2017. Alzheimers Dement (N Y). May 24, 2017;3(3):367-384.
De Felice et al., Abeta oligomers induce neuronal oxidative stress through an N-methyl-D-aspartate receptor-dependent mechanism that is blocked by the Alzheimer drug memantine. J Biol Chem. Apr. 13, 2007;282(15):11590-601.
De Felice et al., Protection of synapses against Alzheimer's-linked toxins: insulin signaling prevents the pathogenic binding of Abeta oligomers. Proc Natl Acad Sci U S A. Feb. 10, 2009;106(6):1971-6.
Dunbar et al., Gene therapy comes of age. Science. Jan. 12, 2018;359(6372):eaan4672.
Durbin et al., Biological Sequence Analysis: Probabilistic Models of Proteins and Nucleic Acids. Cambridge University Press, 2009.
Ferreira et al., The Aβ oligomer hypothesis for synapse failure and memory loss in Alzheimer's disease. Neurobiol Learn Mem. Nov. 2011;96(4):529-43.
Ferrer et al., Neuropathology and pathogenesis of encephalitis following amyloid-beta immunization in Alzheimer's disease. Brain Pathol. Jan. 2004;14(1):11-20.
Figueiredo et al., Memantine rescues transient cognitive impairment caused by high-molecular-weight aβ oligomers but not the persistent impairment induced by low-molecular-weight oligomers. J Neurosci. Jun. 5, 2013;33(23):9626-34.
Franco et al. Successful therapies for Alzheimer's disease: why so many in animal models and none in humans? Frontier in Pharmacology, 2014, 5( 146): 1-13.
Fukumoto et al., High-molecular-weight beta-amyloid oligomers are elevated in cerebrospinal fluid of Alzheimer patients. FASEB J. Aug. 2010;24(8):2716-26.
Fuller et al., New roles for Fc receptors in neurodegeneration-the impact on Immunotherapy for Alzheimer's Disease. Front Neurosci. Aug. 21, 2014;8:235.
Georganopoulou et al., Nanoparticle-based detection in cerebral spinal fluid of a soluble pathogenic biomarker for Alzheimer's disease. Proc Natl Acad Sci U S A. Feb. 15, 2005;102(7):2273-6.
Goeddel, Gene Expression Technology: Methods in Enzymology, vol. 185, Academic Press, San Diego, Calif. (1990).
Gong et al., Alzheimer's disease-affected brain: presence of oligomeric A beta ligands (ADDLs) suggests a molecular basis for reversible memory loss. Proc Natl Acad Sci U S A. Sep. 2, 2003;100(18):10417-22.
Gusfield, Algorithms on Strings, Trees and Sequences, Cambridge University Press, Cambridge UK (1997).
Hayden et al., Amyloid β-protein oligomers and Alzheimer's disease. Alzheimers Res Ther. Nov. 29, 2013;5(6):60.
Holliger et al., Engineered antibody fragments and the rise of single domains. Nat Biotechnol. Sep. 2005;23(9):1126-36.
Huang et al., Single-chain fragment variable passive immunotherapies for neurodegenerative diseases. Int J Mol Sci. Sep. 17, 2013;14(9):19109-27.
Hudson et al., Engineered antibodies. Nat Med. Jan. 2003;9(1):129-34.
Hurdy et al., Therapeutic AAV Gene Transfer to the Nervous System: A Clinical Reality. Neuron Mar. 6, 2019;101(5):839-862.
JÜrgensen et al., Activation of D1/D5 dopamine receptors protects neurons from synapse dysfunction induced by amyloid-beta oligomers. J Biol Chem. Feb. 4, 2011;286(5):3270-6.
Köhler et al., Derivation of specific antibody-producing tissue culture and tumor lines by cell fusion. Eur J Immunol. Jul. 1976;6(7):511-9.
Kussie et al. A Single Engineered Amino Acid Substitution Changes Antibody Fine Specificity. J Immunol 1994, 152(1):146-52.
Lambert et al., Diffusible, nonfibrillar ligands derived from Abeta1-42 are potent central nervous system neurotoxins. Proc Natl Acad Sci U S A. May 26, 1998;95(11):6448-53.
Lambert et al., Monoclonal antibodies that target pathological assemblies of Abeta. J Neurochem. Jan. 2007;100(1):23-35.
Larson et al., Soluble Aβ oligomer production and toxicity. J Neurochem. Jan. 2012;120 Suppl 1(Suppl 1):125-139.
Ledo et al., Amyloid-β oligomers link depressive-like behavior and cognitive deficits in mice. Mol Psychiatry. Oct. 2013;18(10):1053-4.
Livak et al., Analysis of relative gene expression data using real-time quantitative PCR and the 2(-Delta Delta C(T)) Method. Methods. Dec. 2001;25(4):402-8.
Lonberg, Human antibodies from transgenic animals. Nat Biotechnol. Sep. 2005;23(9):1117-25.
Lonberg, Human monoclonal antibodies from transgenic mice. Handb Exp Pharmacol. 2008;181(181):69-97.
Lourenco et al., Exercise-linked FNDC5/irisin rescues synaptic plasticity and memory defects in Alzheimer's model. Jan. 2019;25(1):165-175.
Marks et al., By-passing immunization. Human antibodies from V-gene libraries displayed on phage. J Mol Biol. Dec. 5, 1991;222(3):581-97.
Monnier et al., In Vivo Applications of Single Chain Fv (Variable Domain) (scFv) Fragments. Antibodies 2013, 2(2), 193-208.
Mucke, et al., Neurotoxicity of amyloid B-protein: synaptic and network dysfunction. Cold Spring Harb Perspect Med. Jul. 2012;2(7):a006338.
Nicoll et al., Neuropathology of human Alzheimer disease after immunization with amyloid-beta peptide: a case report. Nat Med. Apr. 2003;9(4):448-52.
Orgogozo et al., Subacute meningoencephalitis in a subset of patients with AD after Abeta42 immunization. Neurology. Jul. 8, 2003;61(1):46-54.
Pattali et al., AAV9 Vector: a Novel modality in gene therapy for spinal muscular atrophy. Gene Ther. Aug. 2019;26(7-8):287-295.
Piton et al., Alzheimer's Disease: Advances in Drug Development. J Alzheimers Dis. 2018;65(1):3-13.
Puzzo et al., Amyloid-beta peptide inhibits activation of the nitric oxide/cGMP/cAMP-responsive element-binding protein pathway during hippocampal synaptic plasticity. J Neurosci. Jul. 20, 2005;25(29):6887-97.
Raffi et al., A phase1 study of stereotactic gene delivery of AAV2-NGF for Alzheimer's disease. Alzheimers Dement. Sep. 2014;10(5):571-81.
Raffi et al., Adeno-Associated Viral Vector (Serotype 2)-Nerve Growth Factor for Patients With Alzheimer Disease: A Randomized Clinical Trial. JAMA Neurol. Jul. 1, 2018;75(7):834-841.
Reardon. Alzheimer's researchers seek better mice Nature, 2018, 563:611-612.
Reitz. Toward precision medicine in Alzheimer's disease Ann transl med 2016, 4(6): 107.
Sambrook et al., Molecular Cloning, a Laboratory Manual, 4th edition, Cold Spring Harbor Press, Cold Spring Harbor, N.Y. 2012.
Schulz et al., Principles of Protein Structure, Springer-Verlag, New York. 1979. vol 118,1. 151-152.
Sebollela et al., A human scFv antibody that targets and neutralizes high molecular weight pathogenic amyloid-β oligomers. J Neurochem. Sep. 2017;142(6):934-947.
Sebollela et al., Amyloid-β oligomers induce differential gene expression in adult human brain slices. J Biol Chem. Mar. 2, 2012;287(10):7436-45.
Selkoe et al., The amyloid hypothesis of Alzheimer's disease at 25 years. EMBO Mol Med. Jun. 1, 2016;8(6):595-608.
Sevigny et al., The antibody aducanumab reduces Aβ plaques in Alzheimer's disease. Nature. Sep. 1, 2016;537(7618):50-6.
Soding, Protein homology detection by HMM-HMM comparison. Bioinformatics. Apr. 1, 2005;21(7):951-60.
Stanford Health Now. Alzheimer's prevention, treatment and research—A Q and A with Dr Frank Longo accessed from Stanfordhealthcare.org on May 3, 2016.

(56) References Cited

OTHER PUBLICATIONS

Tomiyama et al., A mouse model of amyloid beta oligomers: their contribution to synaptic alteration, abnormal tau phosphorylation, glial activation, and neuronal loss in vivo. J Neurosci. Apr. 7, 2010;30(14):4845-56.
Van Dyck, Anti-Amyloid-β Monoclonal Antibodies for Alzheimer's Disease: Pitfalls and Promise. Biol Psychiatry. Feb. 15, 2018;83(4):311-319.
Velasco et al., Synapse-binding subpopulations of Aβ oligomers sensitive to peptide assembly blockers and scFv antibodies. ACS Chem Neurosci. Nov. 21, 2012;3(11):972-81.
Vitek et al. Translational animal models for Alzheimer's disease: An Alzheimer's Association Business Consortium Think Tank Alz Dement, 2020, 6:e12114.

* cited by examiner

FIG. 1A-D
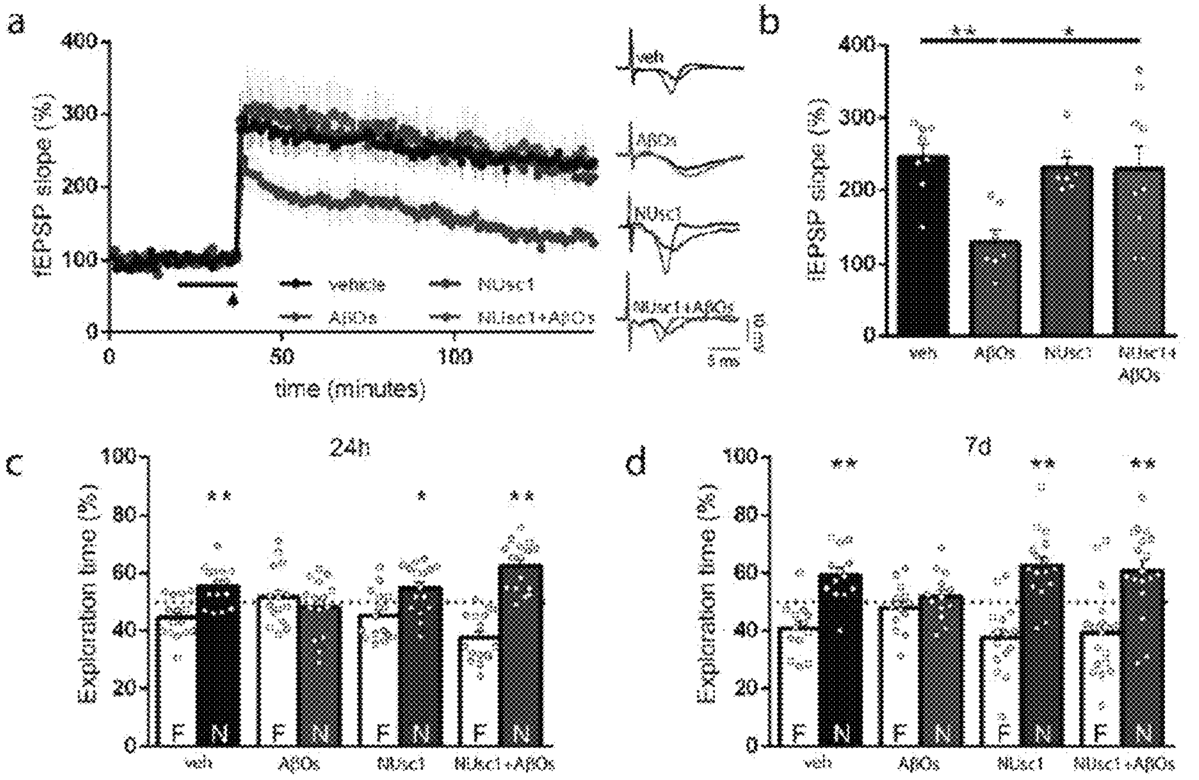

FIG. 3A-E
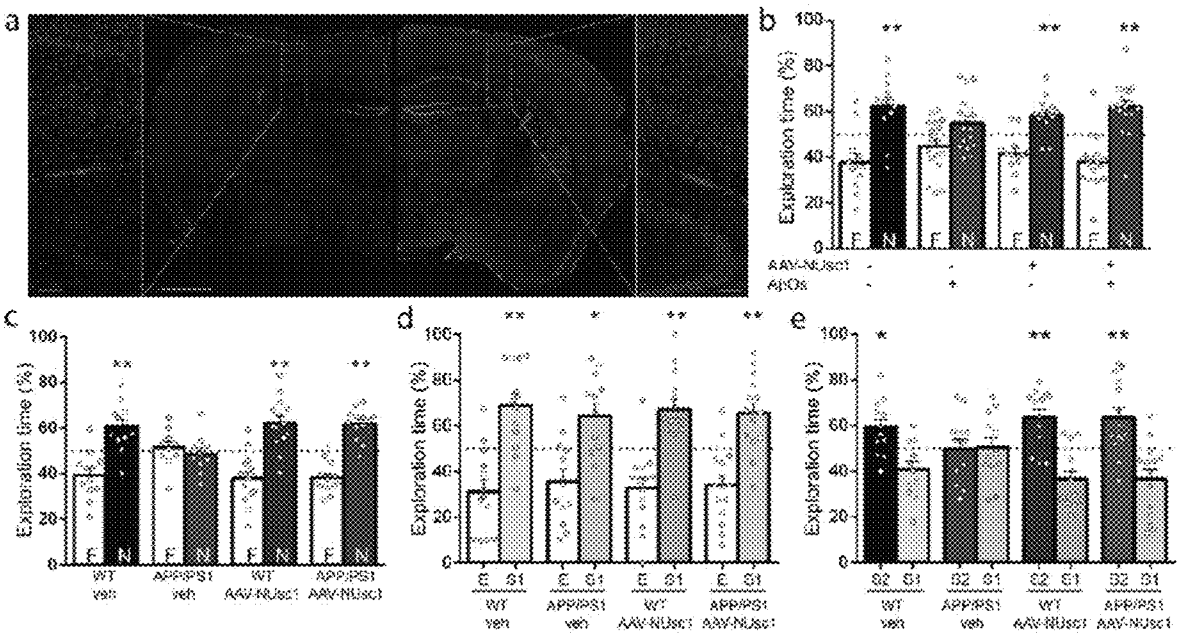

FIG. 6A-B

COMPOSITIONS AND METHODS FOR TREATING ALZHEIMER'S DISEASE

CROSS-REFERENCE TO RELATED APPLICATION

The present invention is a continuation of U.S. patent application Ser. No. 16/820,269, filed Mar. 16, 2020, now U.S. Pat. No. 11,541,086, which claims the benefit of U.S. Provisional Patent Application Ser. No. 62/818,483, filed Mar. 14, 2019, which is hereby incorporated by reference in its entirety.

SEQUENCE LISTING

The text of the computer readable sequence listing filed herewith, titled "36285-304_SEQUENCE_LISTING_ST26", created Jan. 3, 2023, having a file size of 23 bytes, is hereby incorporated by reference in its entirety.

FIELD

Provided herein are antibodies against amyloid-beta (A3) oligomers, and methods of use thereof for the treatment of Alzheimer's disease (AD). In particular, neauronal expression of single-chain variable fragment (scFv) antibodies against Aβ oligomers is provided as a therapeutic approach in the treatment of AD.

BACKGROUND

Alzheimer's disease (AD) is the main cause of dementia in the elderly and is characterized by abnormal accumulation of the amyloid-beta peptide (Ab) in the brain.

SUMMARY

Provided herein are antibodies against amyloid-beta (A3) oligomers, and methods of use thereof for the treatment of Alzheimer's disease (AD). In particular, neauronal expression of single-chain variable fragment (scFv) antibodies against Aβ oligomers is provided as a therapeutic approach in the treatment of AD.

In some embodiments, provided herein are compositions comprising an engineered adeno-associated virus (AAV) comprising a nucleic acid vector comprising a polynucleotide encoding an NUsc1 antibody or antibody fragment. In some embodiments, the NUsc1 antibody or antibody fragment is a single-chain variable fragment (ScFv). In some embodiments, the ScFv comprises at least 70% (e.g., >70%, >75%, >80%, >85%, >90%, >95%, etc.) sequence identity with SEQ ID NO: 4. In some embodiments, the polynucleotide comprises 70% (e.g., >70%, >75%, >80%, >85%, >90%, >95%, etc.) sequence identity with SEQ ID NO: 3. In some embodiments, the ScFv comprises: (a) a heavy chain variable region comprising a complementarity determining region 1 (CDR) amino acid sequence of SEQ ID NO: 5, a CDR2 amino acid sequence of SEQ ID NO: 6, and a CDR3 amino acid sequence of SEQ ID NO: 7, and (b) a light chain variable region comprising a CDR1 amino acid sequence of SEQ ID NO: 8, a CDR2 amino acid sequence of SEQ ID NO: 9, and a CDR3 amino acid sequence of SEQ ID NO: 10. In some embodiments, the ScFv binds the same epitope as an antibody of SEQ ID NO: 3.

In some embodiments, provided herein are methods of treating or preventing Alzheimer's disease (AD) comprising administering to a subject the pharmaceutical composition comprising an engineered adeno-associated virus (AAV) comprising a nucleic acid vector comprising a polynucleotide encoding an NUsc1 antibody or antibody fragment described herein. In some embodiments, the subject is human. In some embodiments, the subject suffers from AD. In some embodiments, the subject has early stage AD. In some embodiments, methods further comprise co-administering an additional therapeutic agent. In some embodiments, the pharmaceutical preparation is administered by intracerebroventricular injection.

In some embodiments, provided herein are polynucleotides encoding an antibody against amyloid-beta oligomers (AβOs). In some embodiments, the antibody binds the same epitope as NUsc1. In some embodiments, the antibody has an affinity for the epitope of at least $10^7$ $M^{-1}$.

In some embodiments, the antibody comprises the same complementarity-determining regions (CDRs) as NUsc1. In some embodiments, the antibody is an antibody fragment. In some embodiments, the antibody is a single-chain variable fragment (scFv) antibody. In some embodiments, a vector is provided comprising a polynucleotide described herein (e.g., encoding an antibody against AβOs). In some embodiments, the vector is a viral vector. In some embodiments, the viral vector is an adeno-associated virus (AAV). In some embodiments, the viral vector is lentivirus. In some embodiments, the vector is a non-viral vector. In some embodiments, the vector is a human-compatible vector. In some embodiments, provided herein are polypeptides encoded by the polynucleotides and vectors described herein. In some embodiments, provided herein are pharmaceutical preparations comprising the polynucleotides and vectors described herein.

In some embodiments, provided herein are methods of treating or preventing Alzheimer's disease (AD) comprising administering a therapeutic dose of a pharmaceutical preparation described herein to a subject. In some embodiments, the subject is human. In some embodiments, the subject suffers from AD. In some embodiments, the subject has early stage AD. In some embodiments, methods further comprise co-administering an additional therapeutic agent. In some embodiments, the pharmaceutical preparation is administered by intracerebroventricular injection.

In some embodiments, provided herein are methods of treating or preventing Alzheimer's disease (AD) comprising neuronally expressing a therapeutic dose of an antibody against amyloid-beta oligomers (AβOs) to a subject.

BRIEF DESCRIPTION OF THE DRAWINGS

FIG. 1A-D: Recombinant NUsc1 prevents ABO-induced inhibition of long-term potentiation (LTP) in hippocampal slices and memory impairment in mice. (a) Long-term potentiation was measured in mouse hippocampal slices. Baseline responses were recorded for 20 minutes, after which slices were perfused for 20 minutes (black horizontal line) with vehicle, purified recombinant NUsc1 (200 pM), AβOs (200 nM), or NUsc1+AβOs. LTP was elicited by high-frequency stimulation (black arrowhead) at CAβ (Schaeffer collaterals) and recording at CA1 for two hours after stimulus. The main plot shows field excitatory postsynaptic potentials (fEPSP) slopes measured as a function of time in different experimental conditions.

Figure 2A:
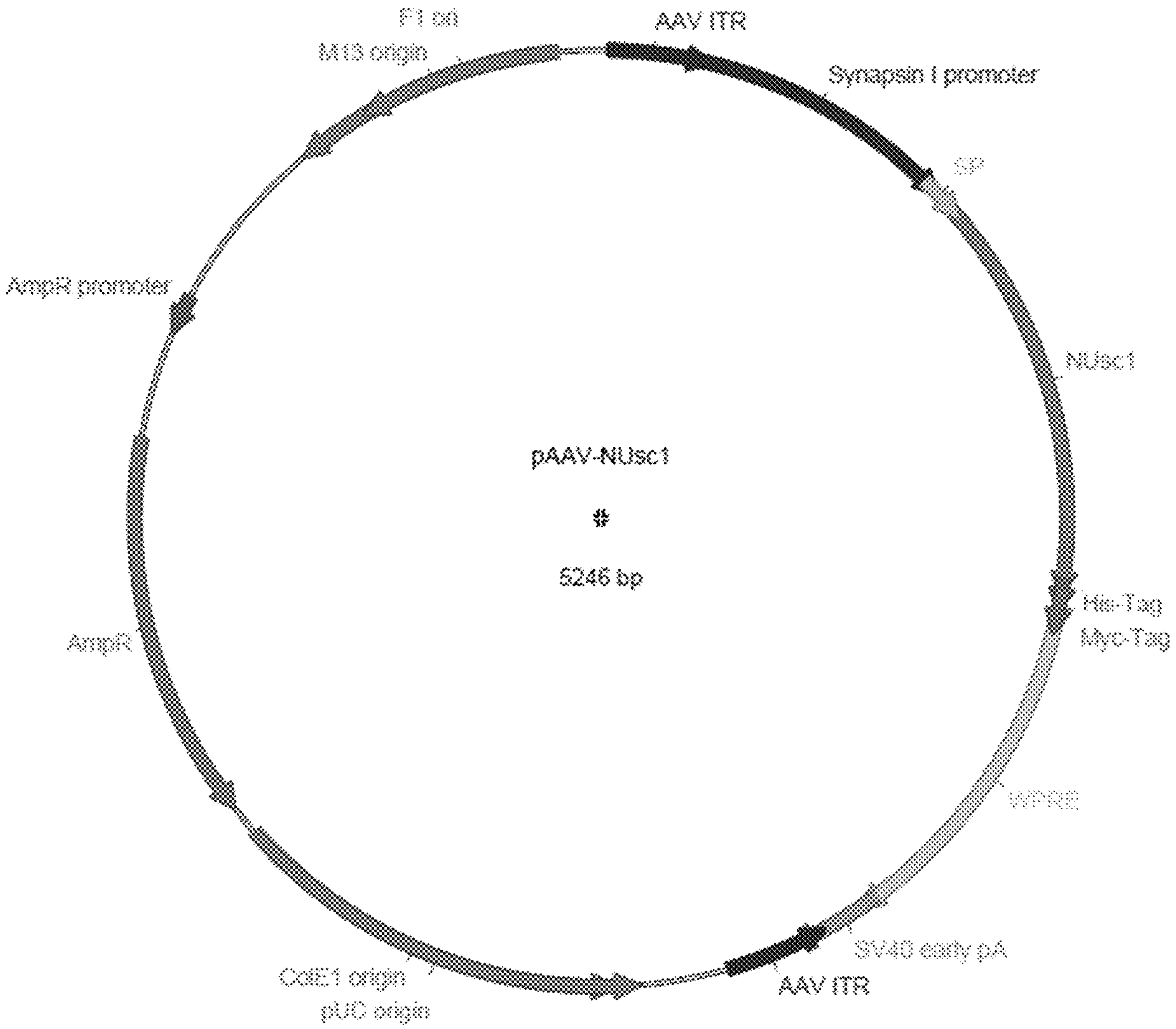

Representative fEPSP traces before (black lines) and after high-frequency stimulus (colored lines) are illustrated on the right for each experimental condition. (b) Plot of mean fEPSP measured two hours after stimulus. N=7-9 slices from 5-7 individual mice per experimental condition. Symbols represent individual slices. *$p<0.05$, **$p<0.01$, Two-way ANOVA followed by Dunnett's post-hoc test. (c-d) NUsc1 prevents ABO-induced memory impairment in mice. Three-month-old Swiss mice received an i.c.v. infusion of NUsc1 (10 fmol) 30 minutes prior to i.c.v. infusion of AβOs (10 pmol). Animals were tested in the Novel Object Recognition (NOR) task 24 hours (c) and 7 days (d) after ABO infusion. Percentages of time spent exploring the novel object are represented by colored bars. $^{*}p<0.05$, $^{**}p<0.01$, one-sample Student's t-test comparing the % of novel object exploration time to the chance value of 50%. Symbols represent individual mice. Color coding is the same in all panels.

FIG. 2: Transduction by AAV-NUsc1 drives NUsc1 expression and secretion by adult human brain slices, decreases AβO binding and prevents dendritic spine loss in rat hippocampal neurons. (a) Map of the pAAV-NUsc1 plasmid used for AAV-NUsc1 vector production. The heavy and light chains of NUsc1 are linked by a flexible linker (VH/linker/VK). NUsc1 has a Signal Peptide (SP) for secretion and two C-terminal (His and Myc) epitope tags. Expression is under control of neuron-specific promoter synapsin I, and the WPRE domain enhances NUsc1 expression. (b) AAV-NUsc1 drives NUsc1 expression in adult human brain slices in culture. Human cortical slices were infected at 3 days in vitro (DIV) with increasing doses of AAV-NUsc1 vector. At 7 DIV, slices were collected, NUsc1 expression was quantified by qPCR, normalized by 18S ribosomal RNA and plotted as a function of viral particle load per mg tissue. Symbols represent individually treated slices (c) Dot immunoblot (anti-His antibody) analysis of control or AAV-NUsc1-infected ($10^8$ vp/mg) human brain slices. Results for homogenized tissue (top) or culture medium (bottom) are shown. (d) Hippocampal cultures were transduced (or not) with AAV-NUsc1 (MOI=$10^4$) at 14 DIV and exposed to AβOs (500 nM) at 20 DIV. AβO binding to neurons was detected using oligomer-specific NU4 monoclonal antibody (40) following 3 hours of exposure to AβOs. Representative images are shown for cultures exposed to AβOs (left) or to AβOs after transduction by AAV-NUsc1 (right). Graph shows integrated fluorescence of bound AβOs (NU4 immunoreactivity, puncta along dendrites). Bars represent means±SEM of 5 experiments (normalized for cultures exposed to AβOs alone) with independent cultures and AβO preparations. Symbols correspond to individual cultures. p=0.0056, paired Student's t-test. (e) Hippocampal cultures were transduced (or not) with AAV-NUsc1 (MOI=$10^4$) at 14 DIV and exposed to AβOs (500 nM) at 20 DIV. Dendritic spine density was assessed by Alexa488-phalloidin labeling following 24 hours of exposure to AβOs. Representative images are shown for vehicle- or AβO-exposed cultures that had (or not) been previously transduced by AAV-NUsc1, as indicated in the panels. Insets show zoom images of isolated dendrite segments. The number of dendritic spines along 20 μm dendrite segments was quantified. Three dendrite segments from 5 neurons were quantified in triplicate experiments in each experimental condition. Bars represent means±SEM, N=3 experiments with independent neuronal cultures and AβO preparations; symbols represent independent cultures; p=0.019, Two-way ANOVA followed by Dunnett's multiple comparisons test.

FIG. 3A-E: Transduction by AAV-NUsc1 prevents AβO-induced memory loss and reverses memory and social recognition deficits in aged APPswe/PS1AE9 mice. (a) AAV-mCherry ($3\times10^9$ viral particles) was infused via i.c.v. in 3-month-old Swiss mice. Brain distribution and expression of mCherry were evaluated by immunohistochemistry 8 weeks after infusion. The main image shows a photomontage of coronal sections (−1.82 mm from Bregma) from a control, non-infected mouse (left hemisphere) and an AAV-mCherry-transduced mouse (right hemisphere). Insets show higher magnification images of areas contained within dashed rectangles. (b) Three-month-old Swiss mice received an i.c.v. infusion of $3\times10^9$ viral particles of AAV-NUsc1 8 weeks prior to i.c.v. infusion of AβOs (10 pmol). Animals were tested in the NOR task 24 hours after infusion of AβOs. Percentages of time spent exploring the novel object are represented by colored bars. Symbols correspond to individual mice. (c-e) APPswe/PS1AE9 mice (9-18 month-old male and female mice) received an i.c.v. infusion of $3\times10^9$ AAV-NUsc1 particles. Eight weeks after infection, mice were tested in the NOR task and in the three-chambered social test. (c) Percentages of time spent exploring the novel object in the NOR test are represented by colored bars. Symbols represent data for individual mice. (d) In the three-chambered social test, animals were first habituated in the middle chamber of the apparatus and were then given an option between exploring an empty chamber or a chamber containing a stranger mouse of the same sex and similar age (white bars labeled "E" or colored bars labeled "S1" in the graph, respectively). Symbols represent individual mice. (e) In the social novelty part of the task, mice were given the option to explore the already familiar mouse (S1) or a novel mouse (S2). Time spent exploring novel (dark bars) and familiar (light bars, color-coded as in d) mice was quantified. Symbols represent individual mice. $^{*}p<0.05$, $^{**}p<0.01$, one-sample Student's t-test comparing % of exploration time of the novel mouse (S2) to the chance value of 50%.

Figure 4:
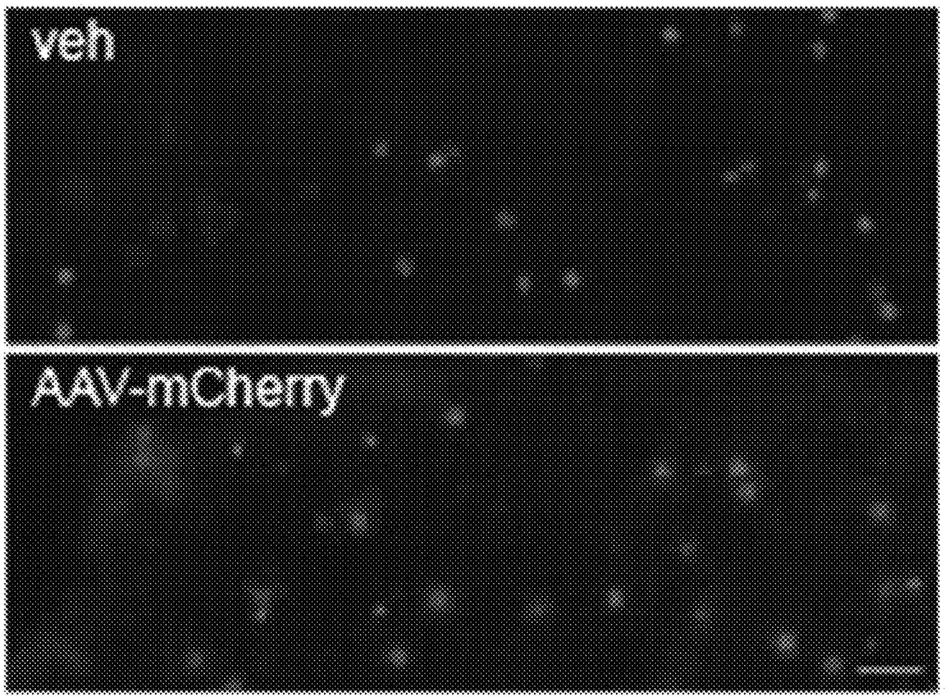

FIG. 4: Human adult cortical slices were infected with $10^8$ vp/mg of AAV-mCherry. mCherry fluorescence was detected by immunohistochemistry. Control (upper pannel) or AAV-mCherry-transduced (lower panel) human slices were imaged at 40×.

Figure 5:
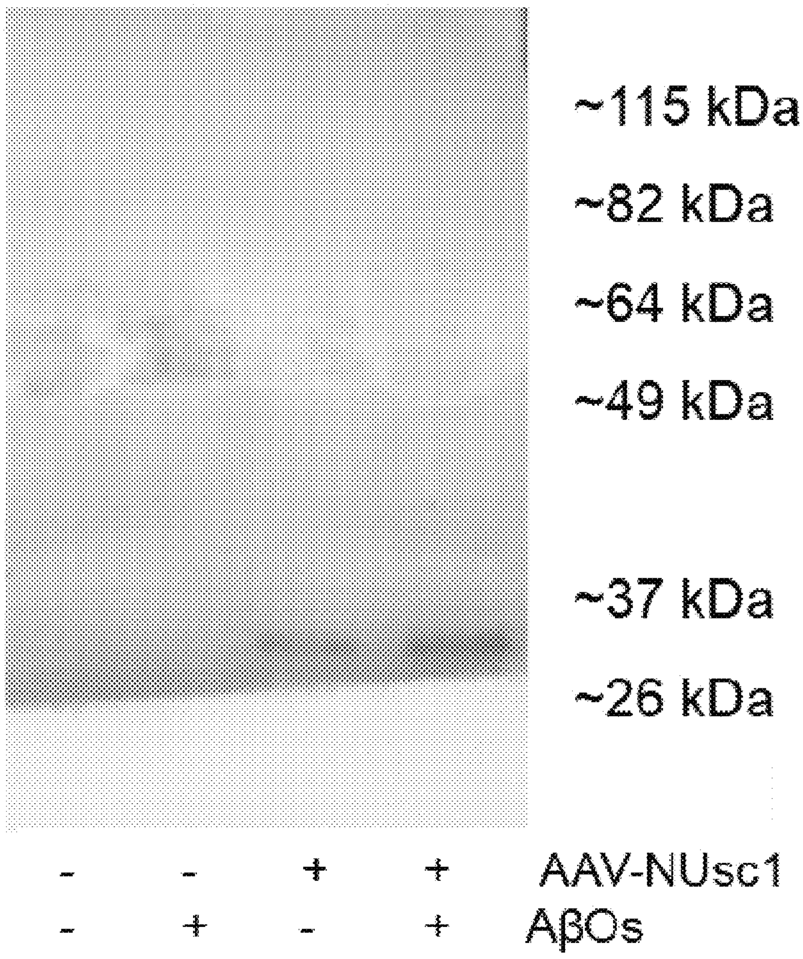

FIG. 5: Western blot of culture media from rat hippocampal neuronal cultures transduced using a MOI of $10^4$ AAV-NUsc1 vp/cell. NUsc1 (~30 kDa) was detected with anti-His antibody.

FIG. 6A-B: (a) qPCR and (b) Western blot showing NUsc1 expression in the brains of WT mice that received an i.c.v. infusion of $3\times10^9$ vp of AAV-NUsc1.

Figure 7:
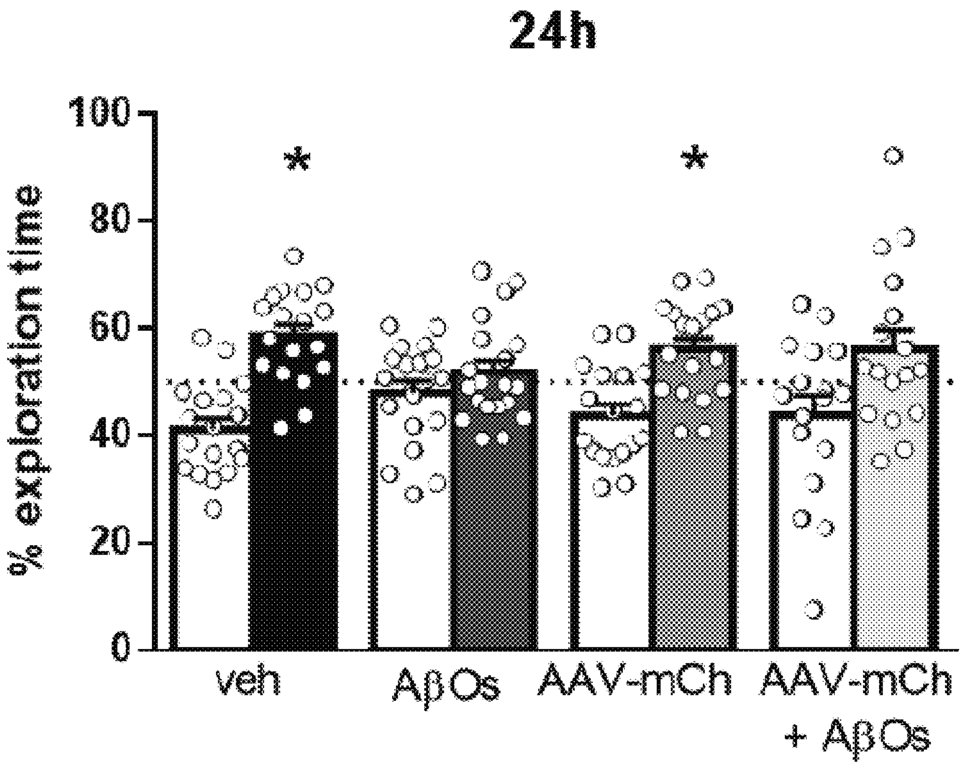

FIG. 7: Transduction by AAV-mCherry does not protect mice from AβO-mediated memory loss. Three-month-old Swiss mice received an i.c.v. infusion of $3\times10^9$ viral particles of AAV-mCherry 8 weeks prior to i.c.v. infusion of AβOs (10 pmol). Animals were tested in the NOR task 24 hours after infusion of AβOs. The percentages of time spent exploring the novel object are represented by colored bars. * $p<0.05$, one-sample Student's t-test comparing % of time spent exploring the novel object to the chance value of 50%.

Definitions

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms “a”, “an” and “the” include plural reference unless the context clearly dictates otherwise. Thus, for example, reference to “an antibody” is a reference to one or more antibodies and equivalents thereof known to those skilled in the art, and so forth.

As used herein, the term “and/or” includes any and all combinations of listed items, including any of the listed items individually. For example, “A, B, and/or C” encompasses A, B, C, AB, AC, BC, and ABC, each of which is to be considered separately described by the statement “A, B, and/or C.”

As used herein, the term “comprise” and linguistic variations thereof denote the presence of recited feature(s), element(s), method step(s), etc. without the exclusion of the presence of additional feature(s), element(s), method step(s), etc. Conversely, the term “consisting of” and linguistic variations thereof, denotes the presence of recited feature(s), element(s), method step(s), etc. and excludes any unrecited feature(s), element(s), method step(s), etc., except for ordinarily-associated impurities. The phrase “consisting essentially of” denotes the recited feature(s), element(s), method step(s), etc. and any additional feature(s), element(s), method step(s), etc. that do not materially affect the basic nature of the composition, system, or method. Many embodiments herein are described using open “comprising” language. Such embodiments encompass multiple closed “consisting of” and/or “consisting essentially of” embodiments, which may alternatively be claimed or described using such language.

As used herein, the term “antibody” refers to a whole antibody molecule or a fragment thereof (e.g., fragments such as scFv, Fab, Fab', and F(ab')2), unless specified otherwise; an antibody may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term “CDR” refers to a CDR from either the light or heavy chain, unless otherwise specified.

As used herein, the term “heavy chain” refers to a polypeptide comprising sufficient heavy chain variable region sequence to confer antigen specificity either alone or in combination with a light chain.

As used herein, the term “light chain” refers to a polypeptide comprising sufficient light chain variable region sequence to confer antigen specificity either alone or in combination with a heavy chain.

As used herein, when an antibody or other entity “specifically recognizes” or “specifically binds” an antigen or epitope, it preferentially recognizes the antigen in a complex mixture of proteins and/or macromolecules, and binds the antigen or epitope with affinity which is substantially higher than to other entities not displaying the antigen or epitope. In this regard, “affinity which is substantially higher” means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>0^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

As used herein, the term “antibody fragment” refers to a portion of a full-length antibody, including at least a portion antigen binding region or a variable region. Antibody fragments include, but are not limited to, Fab, Fab', $F(ab')_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a “Fab” fragment comprises one light chain and the $C_{H1}$ and variable region of one heavy chain. The heavy chain of a Fab molecule cannot form a disulfide bond with another heavy chain molecule. A “Fab” fragment comprises one light chain and one heavy chain that comprises additional constant region, extending between the $C_{H1}$ and $C_{H2}$ domains. An interchain disulfide bond can be formed between two heavy chains of a Fab' fragment to form a “$F(ab')_2$” molecule.

An “Fv” fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946, 778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position. In some embodiments, peptides or polypeptides herein comprise a minimum sequence identity to a base sequence.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

Provided herein are antibodies against amyloid-beta (A3) oligomers, and methods of use thereof for the treatment of Alzheimer's disease (AD). In particular, neauronal expression of single-chain variable fragment (scFv) antibodies against Aβ oligomers is provided as a therapeutic approach in the treatment of AD.

Brain accumulation of the amyloid-β peptide (A3) is a hallmark of Alzheimer's disease (AD), and soluble Aβ oligomers (AβOs) have been implicated in synapse failure and memory impairment in AD (Refs. 1-3; incorporated by reference in its entirety). Experiments conducted during development of embodiments herein demonstrate that treatment with NUsc1, a single-chain variable fragment (scFv) antibody that targets toxic AβOs (Ref. 4; incorporated by reference in its entirety), prevents the inhibition of long-term potentiation in hippocampal slices and memory impairment induced by AβOs in mice. As a therapeutic alternative to intravenous antibody injections, an adeno-associated virus vector was developed to drive neuronal expression of NUsc1 (AAV-NUsc1) within the brain. Transduction by AAV-NUsc1 induced NUsc1 expression and secretion in adult human brain slices, and inhibited AβO binding and resultant dendritic spine loss in primary rat hippocampal cultures. Treatment of mice with AAV-NUsc1 prevented memory impairment induced by AβOs and reversed memory deficits in APPswe/PS1AE9 transgenic AD mice. These results demonstrate the feasibility of gene-mediated AD immunotherapy using single-chain antibodies.

AD is the main form of dementia in the elderly and afflicts over 35 million people worldwide Ref. 5; incorporated by reference in its entirety). Despite remarkable efforts stimulated by the appeal of the amyloid cascade, no disease-modifying drugs have been developed for AD to date (Ref. 6; incorporated by reference in its entirety). However, a distinct therapeutic target that is closely related to the amyloid cascade has emerged in recent years, comprising neurotoxic amyloid beta oligomers (AβOs). A considerable body of evidence implicates AβOs as causal agents of synapse damage and cognitive impairment in AD (Ref. 1-3; incorporated by reference in their entireties). AβOs accumulate in AD brain and CSF (Refs. 7-13; incorporated by reference in their entireties) and are prominent in various transgenic AD animal models, including those with little or no amyloid plaque burden (Refs. 9-10; incorporated by reference in their entireties). Experimental exposure to AβOs causes cognitive deficits and induces major features of AD pathology, including tau hyperphosphorylation, synapse elimination, selective nerve cell death, and brain inflammation (Ref. 1; incorporated by reference in its entirety).

Experiments conducted during development of embodiments herein demonstrate the efficacy of targeting AβOs by NUsc1, an AβO-specific antibody selected by phage display from a library of human-derived single-chain variable fragment (scFv) antibodies. NUsc1 targets a specific subpopulation of AβOs that is highly toxic to synapses, and shows little or no interaction with insoluble amyloid fibrils that are characteristically deposited as plaques in AD brains (Refs. 4, 15; incorporated by reference in their entireties). An important feature of scFv antibodies is their lack of the Fc domain, which reduces the capacity to activate cellular immunity (Refs. 20-22; incorporated by reference in their entireties). A significant adverse effect in clinical trials of immunoglobulin-based AD immunotherapies has been encephalitis, attributed to aberrant activation of cellular immune response triggered by Fc receptors (Refs. 16-19; incorporated by reference in their entireties). In addition, the reduced molecular mass of scFvs compared to intact immunoglobulins facilitates their gene delivery by AAV-based vectors.

Gene-mediated expression of therapeutic antibodies obviates the need for regimens of repeated injections in patients (Refs. 21-22; incorporated by reference in their entireties) and allows for local production of antibodies, thus reducing loss associated to inefficient BBB crossing and systemic clearance mechanisms. AAV vectors are commercially available for use in gene therapy (Ref. 23; incorporated by reference in its entirety).

In some embodiments, provided herein is a viral vector (e.g., lentiviral vector, Adeno-associated virus (AAV) vector (e.g., an AAV9 vector, etc.), etc.), that drives neuronal expression of NUsc1 within the brain.

Experiments were conducted during development of embodiments herein to determine whether exogenous NUsc1 blocks the inhibition of hippocampal long-term potentiation (LTP) and memory loss induced by AβOs. Mouse hippocampal slices were exposed to 200 nM AβOs and measured LTP responses elicited by high-frequency stimulation in Schaeffer collaterals. LTP was markedly inhibited in hippocampal slices exposed to AβOs. In contrast, slices that were treated with NUsc1 before application of AβOs exhibited normal LTP (FIG. 1*a,b*). Control measurements showed that NUsc1 had no effect on LTP in control hippocampal slices. To determine whether NUsc1 could prevent memory impairment induced by AβOs, mice were treated with NUsc1 via an intracerebroventricular (i.e.v.) infusion 30 minutes before i.e.v. administration of AβOs and assessed memory using the Novel Object Recognition (NOR) task. AβO-infused mice exhibited memory impairment both 24 hours and 7 days after AβO infusion (FIG. 1*c, d*). In contrast, mice treated with NUsc1 exhibited normal performance in the NOR test both 24 h and 7 days post-infusion of AβOs.

Figure 2B:
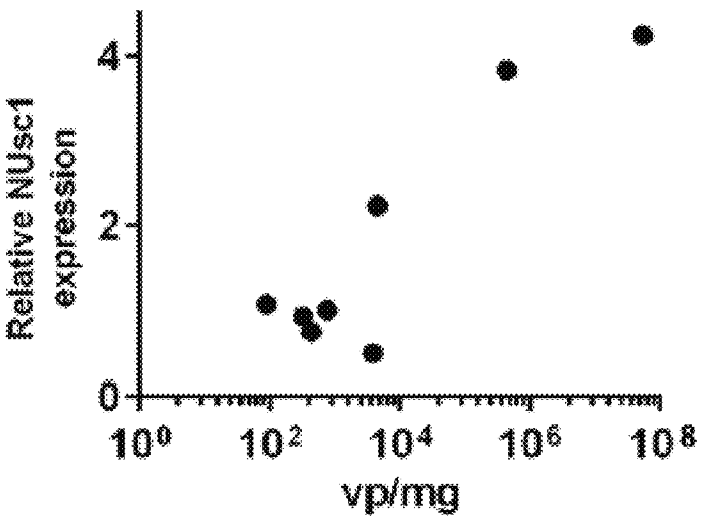
Figure 2C:
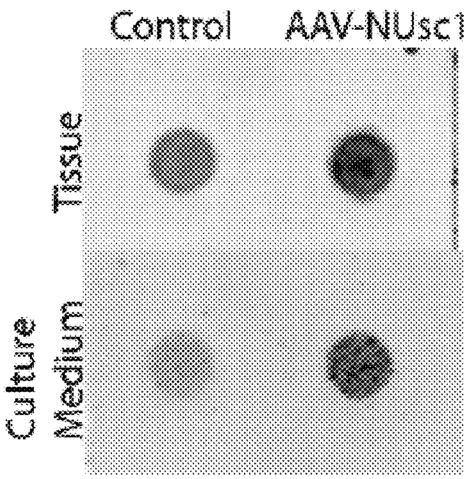

Experiments were conducted during development of embodiments herein to determine whether vector-mediated transduction (e.g., AAV-mediated)) and neuronal expression of NUsc1 is protective in AD models. An AAV9 vector harboring the nucleotide sequence for NUsc1 (with a single amino acid substitution to allow for expression in eukaryotes) was constructed downstream of a signal peptide (SP) for secretory pathway export and under control of the synapsin I promoter for selective neuronal expression (FIG. 2*a*). Neurons were selectively targeted to prevent overexpression of NUsc1 in the brain, thus minimizing the potential for concentration-dependent self-aggregation and for immune or inflammatory responses. To examine the translational potential of AAV-NUsc1 as a therapeutic approach in AD, the capacity of AAV-NUsc1 to drive scFv antibody production in adult human brain tissue was tested. Tests with an AAV9-mCherry control vector confirmed protein expression in human adult cortical slices in culture (FIG. 4). Human cortical slices exposed to increasing titers of AAV-NUsc1 showed dose-dependent expression of NUsc1 (FIG. 2*b*). NUsc1 protein expression and secretion to the medium were confirmed by dot immunoblot analysis (FIG. 2*c*). Results indicate that AAV-NUsc1 transduces adult human neurons and drives the expression and secretion of NUsc1.

Figures 2D, 2E:
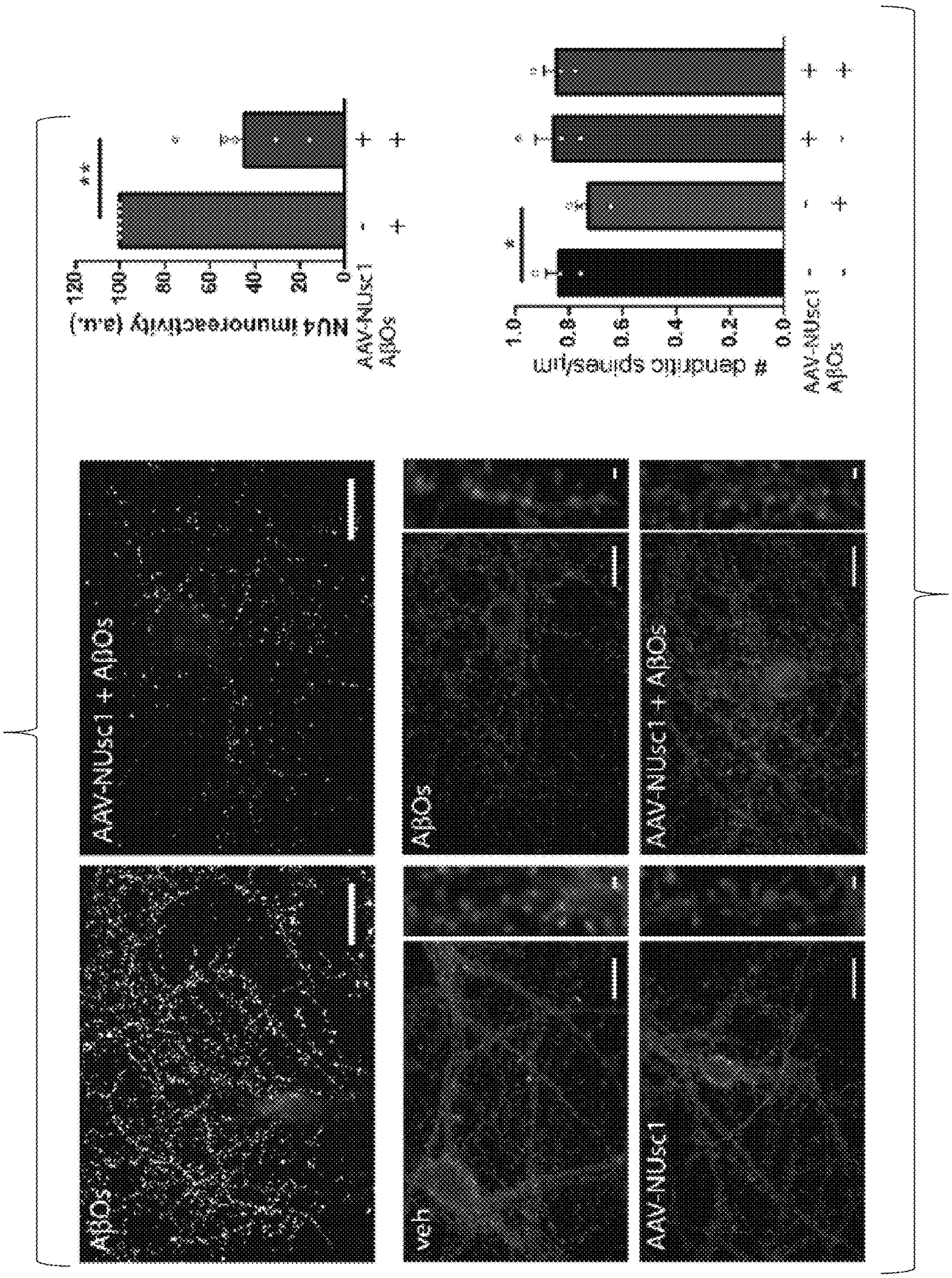

To test AAV-NUsc1 protection of neurons from the toxic impact of AβOs, mature hippocampal cultures (14 DIV) were transduced with AAV-NUsc1. Secretion of NUsc1 to the culture medium was verified by Western blotting at 21 DIV (FIG. 5). Experiments were conducted during development of embodiments herein to determine whether NUsc1 endogenously produced and secreted by AAV-NUsc1-transduced neurons could similarly block neuronal bindings of AβOs. Transduction by AAV-NUsc1 caused~ 50% decrease in AβO binding to dendrites in hippocampal neurons (FIG. 2*d*). It was further investigated whether this reduction in AβO binding would protect neurons from AβO-induced loss of dendritic spines. Neurons exposed to AβOs showed ~15% decrease in dendritic spine density compared to control cultures, while neurons transduced by AAV-NUsc1 prior to exposure to AβOs exhibited normal dendritic spine density (FIG. 2*e*).

Figure 6:
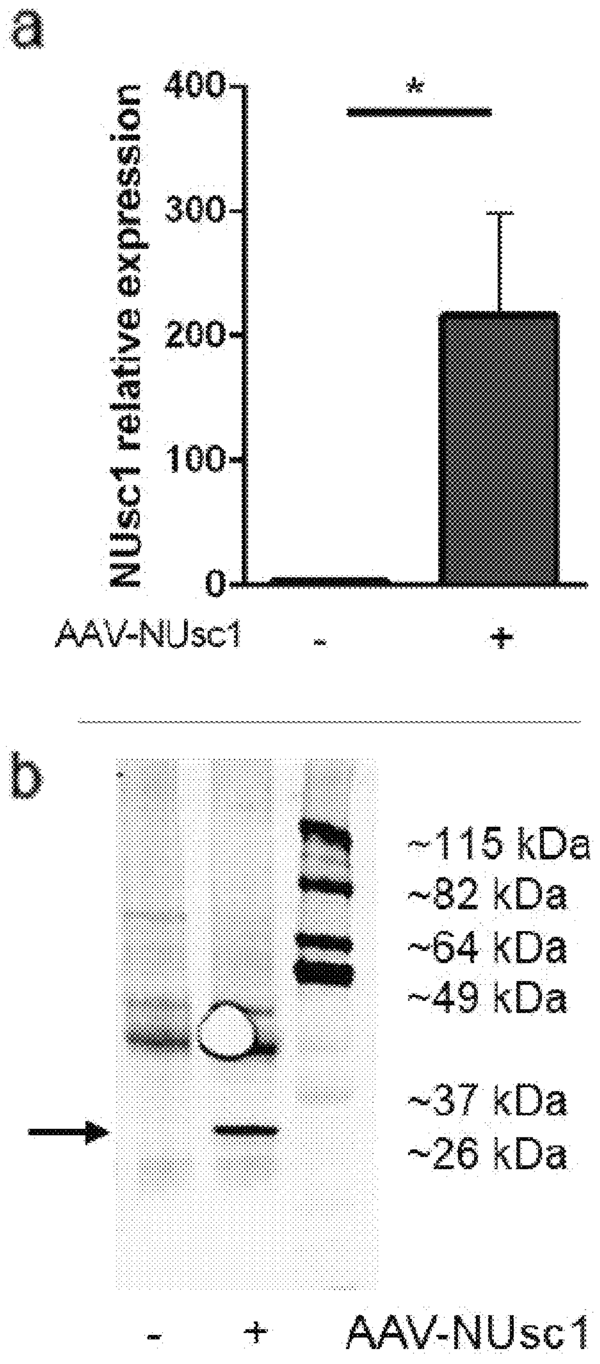

Aiming to assess the in vivo efficacy of AAV9-mediated transduction, brain distribution and neuronal expression of the transgene was examined following i.c.v. infusion of AAV9-mCherry in mice. Results revealed that AAV-mCherry distributed and induced expression of mCherry over the entire mouse brain, with prominent expression in the hippocampus and striatum (FIG. 3*a*). AAV-NUsc1 was then infused i.c.v. in 3 month-old Swiss mice, and verified NUsc1 expression in the brains of AAV-NUsc1-infused animals by qPCR and immunoblotting (FIG. 6). Two months after i.c.v. infusion of AAV-NUsc1 or AAV-mCherry, animals received an i.c.v. infusion of AβOs. When tested in the NOR memory test, both AβO-infused mice (FIG. 3*b*) and AAV-mCherry-treated/AβO-infused mice (FIG. 7) failed the task. In contrast, mice transduced by AAV-NUsc1 exhibited normal performance in the NOR task after infusion of AβOs (FIG. 3*b*). Control experiments showed that transduction by AAV-NUsc1 had no impact on memory performance of control, vehicle-infused mice in the NOR test. Finally, the beneficial action of AAV-NUsc1 on memory impairment exhibited by aged APPswe/PS1AE9 AD model mice was investigated. Memory tests on APPswe/PS1AE9 mice (or WT littermates) were performed two months after i.c.v. infusion of AAV-NUsc1. APPswe/PS1AE9 mice failed both the NOR test and the social memory phase of the three-chambered social recognition test (FIG. 3*c,e*), but not in the sociability phase of the three-chambered test (FIG. 3*d*). Remarkably, APPswe/PS1AE9 mice transduced by AAV-NUsc1 exhibited normal performances in both NOR and social memory tasks (FIG. 3*c,e*). Therefore, it was found that recombinant NUsc1 protected hippocampal slices from LTP inhibition and prevented memory impairment induced by AβOs in mice. Mechanistically, AAV-mediated neuronal expression of NUsc1 reduced AβO binding to neurons and blocked AβO-induced loss of dendritic spines in cultured hippocampal neurons. Transduction by AAV-NUsc1 prevented memory deficits in AβO-infused mice and, notably, reversed memory impairments in aged APPswe/PS1AE9 mice. AAV-NUsc1 effectively transduced and drove the expression and secretion of NUsc1 by adult human brain slices.

Gene therapy recently has attracted considerable interest stemming from its successful introduction in clinical practice for spinal muscular atrophy (Ref. 30; incorporated by reference in its entirety). Moreover, gene therapy has reached clinical trials in a number of neurological disorders, including lysosomal storage diseases, aromatic L-amino acid decarboxylase deficiency disorders and Parkinson's disease (Ref. 31; incorporated by reference in its entirety). Two gene therapy clinical trials have been registered in ClinicalTrials.gov for AD (NCT00087789 and NCT03634007). While the first approach using an AAV2 vector to induce brain NGF expression failed to prevent cognitive impairment in AD patients (Ref. 25; incorporated by reference in its entirety), it showed no adverse effects. The second approach using an AAVrh.10hAPOE2 to treat APOE4 homozygotes is recruiting patients for Phase 1.

Experiments conducted during development of embodiments herein utilize a gene therapy approach to achieve sustained neuronal expression of a human-derived scFv antibody against a specific, highly toxic subpopulation of Aβ oligomers. Experiments conducted during development of embodiments herein demonstrate that this strategy provides protection against AβO-induced memory decline in wild-type mice and to reversal of age-dependent memory impairment in APPswe/Ps1AE9 mice. Advantages include (i) the need for a single i.c.v. infusion of AAV-NUsc1 to achieve sustained expression of NUsc1, (ii) local brain expression and secretion of a single-chain antibody devoid of the Fc domain and, thus, of low immunogenicity, and (iii) specific targeting of a particular subpopulation of AβOs that are highly toxic to synapses and neurons.

Particularly in light of the above, provided herein are antibodies and antibody fragments that bind to AβOs, polynucleotides encoding such antibodies and antibody fragments, vectors (e.g., AAV vectors) comprising such polynucleotides, pharmaceutical preparations comprising such antibodies and antibody fragments, polynucleotides, or vectors, and methods of treating alzheimer's disease in a subject by administering such pharmaceutical preparations. In some embodiments, the antibody or an antigen-binding fragment thereof specifically binds to AβOs.

In some embodiments, the antibody or an antigen-binding fragment thereof disclosed herein comprises (a) a heavy chain variable region comprising a CDR1 amino acid sequence comprising SEQ ID NO: 5, a CDR2 amino acid sequence comprising SEQ ID NO: 6, and a CDR3 amino acid sequence comprising SEQ ID NO: 7 and (b) a light chain variable region comprising a CDR1 amino acid sequence comprising SEQ ID NO: 8, a CDR2 amino acid sequence comprising SEQ ID NO: 9, and a CDR3 amino acid sequence comprising SEQ ID NO: 10. Alternatively, the antibody or antigen-binding fragment thereof may comprise heavy chain variable region CDR1, CDR2, and CDR3 amino acid sequences that are at least 90% identical to SEQ ID NO: 5, SEQ ID NO: 6, and/or SEQ ID NO: 7, respectively, and/or light chain variable region CDR1, CDR2, and CDR3 amino acid sequences that are at least 90% identical to SEQ ID NO: 8, SEQ ID NO: 9, and/or SEQ ID NO: 10, respectively.

In one embodiment, (i) each of the heavy chain variable region CDR1, CDR2, and/or CDR3 amino acid sequences comprises, consists essentially of, or consists of SEQ ID NO: 5, SEQ ID NO: 6, and/or SEQ ID NO: 7, respectively, and (ii) each of the light chain variable region CDR1, CDR2, and/or CDR3 amino acid sequences comprises, consists essentially of, or consists of SEQ ID NO: 8, SEQ ID NO: 9, and/or SEQ ID NO: 10, respectively. When the heavy and/or light chain CDR1, CDR2, and CDR3 of the disclosed antibody consist essentially of the amino acid sequences set forth above, additional components can be included in the CDR that do not materially affect the antibody or antigen-binding fragment thereof (e.g., protein moieties such as biotin that facilitate purification or isolation). When the heavy and/or light chain CDR1, CDR2, and CDR3 of the disclosed antibody consist of the amino acid sequences set forth above, each CDR does not comprise any additional components (i.e., components that are not endogenous to the CDR).

In some embodiments, the antibody or antigen-binding fragment thereof comprises a heavy chain variable region ($V_H$) amino acid sequence comprising, consisting essentially of, or consisting of SEQ ID NO: 11 and a light chain variable region ($V_L$) amino acid sequence comprising, consisting essentially of, or consisting of SEQ ID NO: 12. When the $V_H$ amino acid sequence consists essentially of SEQ ID NO: 11 and the $V_L$ amino acid sequence consists essentially of SEQ ID NO: 12, additional components can be included in the heavy or light chain variable regions that do not materially affect the antibody or antigen-binding fragment thereof (e.g., protein moieties such as biotin that facilitate purification or isolation). When the $V_H$ amino acid sequence consists of SEQ ID NO: 11 and the $V_L$ amino acid sequence consists of SEQ ID NO: 12, the heavy and light chain variable regions do not comprise any additional components (i.e., components that are not endogenous to the heavy or light chain variable region).

The disclosure also provides an antibody or antigen-binding fragment thereof which comprises a heavy chain variable region amino acid sequence that is at least 70% identical (e.g., at least 75%, at least 80%, at least 95%, at least 90%, at least 91%, at least 92%, at least 93%, at least 94%, at least 95%, at least 96%, at least 97%, at least 98%, at least 99%, or 100% identical) to SEQ ID NO: 11 and a light chain variable region amino acid sequence that is at least 70% identical (e.g., at least 75%, at least 80%, at least 95%, at least 90%, at least 91%, at least 92%, at least 93%, at least 94%, at least 95%, at least 96%, at least 97%, at least 98%, at least 99%, or 100% identical) to SEQ ID NO: 12. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer).

A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3×, FAS™, and SSEARCH) (for sequence alignment and sequence similarity searches). Sequence alignment algorithms also are disclosed in, for example, Altschul et al., J. Molecular Biol., 215(3): 403-410 (1990), Beigert et al., *Proc. Natl. Acad. Sci. USA,* 106(10): 3770-3775 (2009), Durbin et al., eds., *Biological Sequence Analysis: Probabilistic Models of Proteins and Nucleic Acids*, Cambridge University Press, Cambridge, UK (2009), Soding, Bioinformatics, 21(7): 951-960 (2005), Altschul et al., *Nucleic Acids Res.,* 25(17): 3389-3402 (1997), and Gusfield, *Algorithms on Strings, Trees and Sequences, Cambridge University Press*, Cambridge UK (1997)).

One or more amino acids of the aforementioned antibody or antigen fragment thereof can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free—$NH_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the antibody or antigen-binding fragment thereof (e.g., insertion into the heavy and/or light chain variable region amino acid sequence). Any number of any suitable amino acids can be inserted into the amino acid sequence of the antibody or antigen-binding fragment thereof. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the antibody or antigen-binding fragment thereof. For example, 1-10 amino acids (e.g., 1, 2, 3, 4, 5, 6, 7, 8, 9, or 10 amino acids) may be inserted into the amino acid sequence of the antibody or antigen-binding fragment thereof. In this respect, the amino acid(s) can be inserted into antibody or antigen-binding fragment thereof in any suitable location. Preferably, the amino acid(s) are inserted into a CDR (e.g., CDR1, CDR2, or CDR3) of the antibody or antigen-binding fragment thereof.

The inventive antibody or antigen-binding fragment thereof is not limited to a polypeptide comprising the specific amino acid sequences described herein. Indeed, the antibody or antigen-binding fragment thereof can comprise any heavy chain polypeptide or light chain polypeptide that competes with the inventive antibody or antigen-binding fragment thereof for binding to tenofovir or a tenofovir derivative. Antibody competition can be assayed using routine peptide competition assays such as, for example, ELISA, Western blot, or immunohistochemistry methods (see, e.g., U.S. Pat. Nos. 4,828,981 and 8,568,992; and Braitbard et al., *Proteome Sci.,* 4: 12 (2006)).

The antibody or antigen-binding fragment thereof described herein may be a monoclonal antibody or a polyclonal antibody. The term "monoclonal antibody," as used herein, refers to an antibody produced by a single clone of B lymphocytes that is directed against a single epitope on an antigen. Monoclonal antibodies typically are produced using hybridoma technology, as first described in Köhler and Milstein, *Eur. J. Immunol.,* 5: 511-519 (1976). Monoclonal antibodies may also be produced using recombinant DNA methods (see, e.g., U.S. Pat. No. 4,816,567), isolated from phage display antibody libraries (see, e.g., Clackson et al. Nature, 352: 624-628 (1991)); and Marks et al., *J. Mol.*

*Biol.,* 222: 581-597 (1991)), or produced from transgenic mice carrying a fully human immunoglobulin system (see, e.g., Lonberg, Nat. Biotechnol., 23(9): 1117-25 (2005), and Lonberg, *Handb. Exp. Pharmacol.,* 181: 69-97 (2008)). In contrast, "polyclonal" antibodies are antibodies that are secreted by different B cell lineages within an animal. Polyclonal antibodies are a collection of immunoglobulin molecules that recognize multiple epitopes on the same antigen. In certain embodiments, the antibody or antigen-binding fragment thereof is a polyclonal antibody.

The disclosure also provides a composition comprising the antibody or antigen-binding fragment thereof described herein. The composition desirably is a pharmaceutically acceptable (e.g., physiologically acceptable) composition, which comprises a carrier, preferably a pharmaceutically acceptable (e.g., physiologically acceptable) carrier, and the antibody or antigen-binding fragment thereof. Any suitable carrier can be used within the context of the disclosure, and such carriers are well known in the art. For example, the composition may contain preservatives, such as, for example, methylparaben, propylparaben, sodium benzoate, and benzalkonium chloride. A mixture of two or more preservatives optionally may be used. In addition, buffering agents may be included in the composition. Suitable buffering agents include, for example, citric acid, sodium citrate, phosphoric acid, potassium phosphate, and various other acids and salts. A mixture of two or more buffering agents optionally may be used. Methods for preparing compositions for pharmaceutical use are known to those skilled in the art and are described in, for example, *Remington: The Science and Practice of Pharmacy*, Lippincott Williams & Wilkins; 21st ed. (May 1, 2005).

The disclosure further provides a nucleic acid sequence encoding the aforementioned antibody or antigen-binding fragment thereof. In certain embodiments, the nucleic acid sequence is in the form of a vector. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 4th edition, Cold Spring Harbor Press, Cold Spring Harbor, N.Y. (2012), and Ausubel et al., *Current Protocols in Molecular Biology*, Greene Publishing Associates and John Wiley & Sons, New York, N.Y. (1994)).

In addition to the nucleic acid encoding the antibody or antigen-binding fragment thereof, the vector desirably comprises expression control sequences, such as promoters, enhancers, polyadenylation signals, transcription terminators, internal ribosome entry sites (IRES), and the like, that provide for the expression of the antibody-encoding nucleic sequence in a host cell. Exemplary expression control sequences are known in the art and described in, for example, Goeddel, Gene Expression Technology: Methods in Enzymology, Vol. 185, Academic Press, San Diego, Calif. (1990).

EXPERIMENTAL

Methods

Expression and purification of NUsc1: NUsc1 was expressed in the HB2151 *E. coli* strain with IPTG (Isopropyl b-D-1-thiogalactopyranoside) induction (Ref. 4; incorporated by reference in its entirety). Soluble NUsc1 was purefied from both the supernatant and lysate of HB2151 cells using a Protein A affinity column (GE). The solution containing eluted antibody was buffer-exchanged into phosphate-buffered saline (PBS) (Dulbecco's PBS without calcium or magnesium; Corning), pH 7.4, and concentrated using 10-kDa cutoff centricons (Merck) before storage at −80° C. The final concentration of purified protein was determined using Bradford reagent (BioRad). Purified NUsc1 was routinely checked by SDS-PAGE and SEC (size-exclusion chromatography).

AAV-NUsc1 and AAV-mCherry vectors: NUsc1 scFv was subcloned from the original plasmid for expression in bacteria (piT2-NUsc1) by PCR with the following alternative pairs of primers: PCR1: FWD1 (5'-3') TATTACTCGCGGCCCAGC(SEQ ID NO: 13)/REV1 (5'-3') CTATGCGGCCCCATTCAG (SEQ ID NO: 14). PCR2: FWD2: (5'-3') GCTAGCTATTACTCGCGGCCCAGC (SEQ ID NO: 15) (with a restriction site for Nhel)/REV2: (5'-3') TCGCGACTATGCGGCCCCATTCAG (SEQ ID NO: 16) (with a restriction site for Nrul). The PBSKII plasmid was digested with SmaI and used to link the product of each PCR, yielding intermediate plasmids PBSKII-NUsc1 PCR1 and PBSKII-NUsc1 PCR2. The PBSKII-NUsc1 PCR2 plasmid was digested with Nrul, blunt-ended with Klenow polymerase and digested with Nhel, thus releasing the fragment coding for the open reading frame of NUsc1. This fragment was then cloned into plasmid pA-EAU2 (34) to generate intermediate plasmid pA2-NUsc1, in which NUsc1 is driven by the HCMV promoter. Sequencing of this plasmid revealed a STOP codon between heavy and light chain sequences, which is methylated in bacteria. Since this STOP codon would lead to translation interruption in mammalian cells, site-directed mutagenesis was conducted to replace the STOP codon by a glutamic acid (Glu) codon, resulting in the pA2-NUsc1 plasmid for NUsc1 expression in eukaryotic cells. The NUsc1 protein was then fused to two N-terminal epitope tags (His and Myc tags). In addition, an export signal (SP) was added to promote secretion to the extracellular medium. Finally, the NUsc1 ORF was extracted from pA2-NUsc1 and subcloned into the pBS plasmid to obtain plasmid pBS-NUsc1, in which the NUsc1 ORF is driven by the synapsin I promoter. This plasmid also contains a WPRE sequence to enhance NUsc1 expression (FIG. 2*a*). AAV9 vector production was achieved by co-transfection of 293 cells with pBS-NUsc1, helper plasmid and rep-cap plasmid. Cells were collected 48 h post-transfection and lysed to harvest AAV particles, which were purified by CsCl gradients. Following transduction of mammalian cells, the AAV-NUsc1 vector drives expression of a 30 kDa protein, as expected for the NUsc1 transgene.

Preparation and characterization of AβOs: AβOs were prepared from synthetic AP1_42 (California Peptide) (Refs 35-36; incorporated by reference in their entireties). Oligomer preparations were routinely characterized by size exclusion HPLC and Western blots using oligomer-sensitive NU4 monoclonal antibody (Ref. 40; incorporated by reference in its entirety), and comprised a mixture of Aβ dimers, trimers, tetramers, and higher molecular weight oligomers (Refs. 26, 37, 28; incorporated by reference in their entireties). Protein concentration was determined using the BCA assay (Thermo-Pierce).

Neuronal cultures: Hippocampal cultures were prepared from E18 Wistar rat embryos and were maintained in Neurobasal medium supplemented with B27 (Invitrogen) for 3 weeks as described (38). Cultures were treated with vehicle or AAV-NUsc1 vector using a MOI of $10^4$ at 14 DIV, and were exposed to 500 nM AβOs (or vehicle) at 20 DIV. The supernatant was collected at 21 DIV for determination of the presence of NUsc1 by Western blotting.

Immunocytochemistry and phalloidin labeling: Cells were fixed and blocked (Ref. 39; incorporated by reference in its entirety), incubated with AβO-selective NU4 mouse monoclonal antibody (1 μg/mL; 40) overnight at 4° C., and incubated for 3 h at 23° C. with Alexa conjugated secondary antibody. Spines were labeled with Alexa conjugated phalloidin (which binds to spine-localized dense bundles of F-actin) for 20 min at 23° C., according to manufacturer's instructions (Invitrogen). Coverslips mounted with Prolong containing DAPI were imaged on a Zeiss Axio Observer Z1 microscope.

Electrophysiological recordings: Electrophysiological recordings were performed (Ref. 41; incorporated by reference in its entirety). Transverse hippocampal slices (400 μm) were cut and transferred to a recording chamber where they were maintained at 29° C. and perfused with ACSF (2 ml/min flow rate) continuously bubbled with 95% 02 and 5% CO2. Field extracellular recordings were performed by stimulating the Schaeffer collateral fibers through a bipolar tungsten electrode and recording in CA1 stratum *radiatum* with a glass pipette filled with ACSF. After evaluation of basal synaptic transmission, a 20 min baseline was recorded every minute at an intensity eliciting a response approximately 35% of the maximum evoked response. Slices were then perfused for 20 min with vehicle, 200 nM AβOs, 200 pM NUsc1, or AβOs+NUsc1. After treatments, LTP was induced by theta-burst stimulation (4 pulses at 100 Hz, with bursts repeated at 5 Hz, and three tetanic 10-burst trains at 15 s intervals). Responses were recorded for 2 h after tetanization and were measured as field excitatory postsynaptic potentials (fEPSP) slopes expressed as percentages of baseline.

Human cortical slice culture: Cortical tissue was obtained from adult patients submitted to amygdalo-hippocampectomy for the treatment of refractory temporal lobe epilepsy at the University Hospital of the Federal University of Rio de Janeiro. Collection of this tissue for research purposes was approved by the Institutional IRB of the Federal University of the State of Rio de Janeiro under #CAAE: 69409617.9.0000.5258. A fragment of temporal cortex (surgical access tissue) was collected at the operating room, and was immediately processed and cultured (Ref. 37; incorporated by reference in its entirety). Tissue was sliced at 400 μm using a McIlwain Tissue Chopper. Slices were plated in 24-well plates (1 slice/well) containing 400 μL Neurobasal A (Gibco) supplemented with 1% Glutamax (Gibco), 1% Penicillin/Streptomycin (Gibco), 2% B27 (Gibco) and 0.25 μg/mL Amphotericin B (Gibco) supplemented with 50 ng/mL BDNF (Sigma Aldrich). Cultures were maintained at 37° C. and 5% $CO_2$.

Dot immunoblots: Frozen samples from tissue and culture media of human cortical slices were thawed, and tissue was homogenized in RIPA buffer containing a phosphatase and protease inhibitor cocktail (Thermo Scientific Pierce). Culture media samples were concentrated using 10-kDa cutoff Amicon Ultra-0.5 mL Centrifugal Filters. Samples (20 μg total protein in 200 μL) were spotted onto a nitrocellulose membrane using a vacuum-assisted dot blot apparatus (Bio-Dot Apparatus 1706545, Bio-Rad). Blots were blocked with 5% BSA in Tween-TBS at room temperature for 2 h and incubated at 4° C. overnight with anti-His antibody (1:200; Sigma Aldrich) in blocking buffer. Membranes were then incubated with anti-mouse secondary antibody conjugated to IRDye 800CW (Licor, Lincoln, NE; 1:10,000) at room temperature for 2 h, imaged on an Odyssey Imaging System (Licor) and analyzed using NIH Image J. The integrated density of each dot was normalized by protein concentration of the corresponding sample.

Animals and intracerebroventricular (i.c.v.) infusions: Three-month-old male Swiss, or 9-18 month-old APPswe/PS1AE9 (or WT $C_{57}$BL/6 littermates) male and female mice were used. Animals were housed in groups of five per cage with free access to food and water, under a 12 h light/dark cycle with controlled room temperature and humidity. All procedures followed the Principles of Laboratory Animal Care from the National Institutes of Health and were approved by the Institutional Animal Care and Use Committee of the Federal University of Rio de Janeiro (protocol #IBqM 136/15) and the University of Western Ontario (protocol #2016-10[4] and #2016-103).

For i.c.v. infusion of AAV-NUsc1, AβOs or vehicle, animals were anesthetized for 7 min with 2.5% isoflurane (Cristilia, Sio Paulo, Brazil) using a vaporizer system and were gently restrained only during the injection procedure. A 2.5-mm-long needle was unilaterally inserted 1 mm to the right of the midline point equidistant from each eye and 1 mm posterior to a line drawn through the anterior base of the eyes (Ref. 28; incorporated by reference in its entirety). Swiss mice received $3\times10^9$ viral particles of AAV-NUsc1 in a final volume of 3 μl 7 days before the infusion of 10 pmol AβOs (or an equivalent volume of vehicle). An AAV-mCherry vector was used in control experiments following the same protocol. When indicated, 1.5 μl of purified NUsc1 (0.01 pmol) were administered 30 minutes before AβOs via the same i.c.v. injection site. Transgenic APPswe/PS1AE9 mice (and WT littermate controls) received $3\times10^9$ viral particles of AAV-NUsc1 via i.c.v. two months before behavioral tests.

Immunohistochemistry: Animals were anesthetized and perfused with saline, followed by 4% paraformaldehyde in 0.1 M phosphate buffer, pH 7.4. Fixed brains were removed, cryoprotected in increasing concentrations of sucrose, frozen in dry ice and stored at −80° C. Coronal sections (40 μm) were obtained on a cryostat (Leica Microsystems) and stored in PBS, pH 7.4. Immunohistochemistry was performed after washing the sections extensively with PBS. Groups of 6 sections per animal were immersed in 0.1% Sudan Black B for 30 minutes, washed three times in PBS and blocked for 2 hours with 0.3% Triton X-100 and 5% BSA in PBS at room temperature. Sections were then incubated overnight with anti-mCherry primary antibody (1:100; ThermoFisher) diluted in PBS, washed and incubated for 2 h with Alexa Fluor 594-conjugated secondary antibody (1:1,000; Life Technologies). After a final washing step, sections were briefly stained with DAPI and mounted with Prolong (ThermoFisher). Images were acquired on a Zeiss Axio Observer Z1 microscope.

Western immunoblots: Forty-eight hours after i.c.v. infusion of AβOs, hippocampi and cortex were dissected and immediately frozen in liquid nitrogen. For total protein extraction, samples were thawed and homogenized in PBS containing a phosphatase and protease inhibitor cocktail (Thermo Scientific Pierce). Protein concentrations were determined using the BCA kit. Samples containing 30 μg protein were resolved in 15% polyacrylamide Tris-glycine gels (Invitrogen) and were electrotransferred to nitrocellulose membranes at 350 mA for 1 h. Blots were incubated with 5% BSA in Tween-TBS at room temperature for 2 h and incubated at 4° C. overnight with anti-His tag primary antibody diluted in blocking buffer. Membranes were then incubated with anti-mouse secondary antibody conjugated to IRDye 800CW (1:10,000) at room temperature for 2 h, imaged using Odyssey@ Imaging System and analyzed using NIH Image J.

RNA extraction and quantitative real-time PCR: Cerebral cortices were homogenized and RNA was extracted using SV total RNA isolation kit (Promega). RNA purity was determined by the 260/280 nm absorbance ratio. One g RNA was used for cDNA synthesis using the High-Capacity cDNA Reverse Transcription Kit (Applied Biosystems). qPCR was performed on an Applied Biosystems 7500 RT-PCR system using the Power SYBR kit (Applied Biosystems). Cycle threshold (Ct) values were used to calculate fold changes in gene expression using the $2^{-\Box\Box Ct}$ method (42). The following primers were used to detect the expression of NUsc1: Forward: TCAGCAGAAACCAGGGAAAG (SEQ ID NO: 17); Reverse: CTGCTGATGGTGAGAGTGAAA (SEQ ID NO: 18). Actin 3 was used as a housekeeping gene for mice samples and primers used were: Forward: 5'TGTGACGTTGACATCCGTAAA3'(SEQ ID NO: 19); Reverse: 5'GTACTTGCGCTCAGGAGGAG3' (SEQ ID NO: 20). Human slices samples were normalized by 18S ribosomal RNA and primers used were: Forward: ATCCCTGAAAAGTTCCAGCA(SEQ ID NO: 21); Reverse: CCCTCTTGGTGAGGTCAATG (SEQ ID NO: 22).

Novel object recognition task: The task was performed in an open field arena measuring 30×30×45 cm (W×L×H). The floor of the arena was divided by lines into nine equal rectangles. Test objects were made of glass or plastic and had different shapes, colors, sizes, and textures. During sessions, objects were fixed to the box to prevent displacement caused by exploratory activity of the animals. Previous tests showed that none of the objects used evoked an innate preference. Before training, each animal was submitted to a 5 min habituation session to freely explore the empty arena. Training consisted of a 5-min session during which animals were placed at the center of the arena in the presence of two identical objects. The amount of time spent exploring each object was recorded. Sniffing and touching the object were considered exploratory behavior. The arena and objects were cleaned thoroughly between trials with 40% ethanol to eliminate olfactory cues. In the test session, performed two hours after training, one of the two objects used in the training session was replaced by a new one. Time spent exploring familiar and novel objects was measured. Results were expressed as percentage of time exploring each object during the test session and were analyzed using a one-sample Student's t-test, comparing the mean exploration time for each object against the fixed (chance) value of 50%. An animal that recognizes the familiar object (i.e., that learns the task) explores the novel object >50% of the total time.

Three chambered social task: Each animal was positioned in a box divided into three equally sized areas and tested along three sessions lasting 5 min each. The first session consisted in free exploration of the middle chamber. The second session evaluated social interaction by quantifying the time spent exploring each side-chamber—one containing a small empty wire cage and the other containing an identical cage containing another mouse of the same sex and age as the test animal inside. Finally, the third session consisted in placing a novel mouse in the empty cage and quantifying the amount of time spent exploring the familiar and novel mice, to evaluate social memory.

SEQUENCES

NUsc1 DNA Sequence (His Tag)

SEQ ID NO: 1 atgaaatacctattgcctacggcagccgctggattgttattactcgcggc
ccagccggccatggccgaggtgcagctgttggagtctgggggaggcttgg
tacagcctggggggtccctgagactctcctgtgcagcctctggattcacc
tttagcagctatgccatgagctgggtccgccaggctccagggaaggggct
ggagtgggtctcagcgatttcgaatgggggtgtggagacagcgtacgcag
actccgtgaagggccggttcaccatctccagagacaattccaagaacacg
ctgtatctgcaaatgaacagcctgagagccgaggacacggccgtatatta
ctgtgcgaaaaatactggttcgtttgactactggggccagggaaccctgg
tcaccgtctcgageggtggaggcggttcaggcggaggtggcagcggcggt
ggcgggtcgacggacatccagatgacccagtctccatcctccctgtctgc
atctgtaggagacagagtcaccatcacttgccgggcaagtcagagcatta
gcagctatttaaattggtatcagcagaaaccagggaaagcccctaagctc
ctgatctatgcggcatcccgtttgcaaagtggggtcccatcaaggttcag
tggcagtggatctgggacagatttcactctcaccatcagcagtctgcaac
ctgaagattttgcaacttactactgtcaacagtcgcaggggaggcctgtg
acgttcggccaagggaccaaggtggaaatcaaacgggcggccgcacatca
tcatcaccatcacg NUsc1 Protein Sequence (His Tag)

SEQ ID NO: 2

MKYLLPTAAAGLLLLAAQPAMAEVQLLESGGGLVQPGGSLRLSCAASGFT
FSSYAMSWVRQAPGKGLEWVSAISNGGVETAYADSVKGRFTISRDNSKNT
LYLQMNSLRAEDTAVYYCAKNTGSFDYWGQGTLVTVSSGGGGSGGGGSGG
GGSTDIQMTQSPSSLSASVGDRVTITCRASQSISSYLNWYQQKPGKAPKL
LIYAASRLQSGVPSRFSGSGSGTDFTLTISSLQPEDFATYYCQQSQGRPV
TFGQGTKVEIKRAAAHREIHHH

NUsc1 DNA Sequence (No His Tag)

SEQ ID NO: 3 atgaaatacctattgcctacggcagccgctggattgttattactcgcggc
ccagccggccatggccgaggtgcagctgttggagtctgggggaggcttgg
tacagcctggggggtccctgagactctcctgtgcagcctctggattcacc
tttagcagctatgccatgagctgggtccgccaggctccagggaaggggct
ggagtgggtctcagcgatttcgaatgggggtgtggagacagcgtacgcag
actccgtgaagggccggttcaccatctccagagacaattccaagaacacg
ctgtatctgcaaatgaacagcctgagagccgaggacacggccgtatatta
ctgtgcgaaaaatactggttcgtttgactactggggccagggaaccctgg
tcaccgtctcgagcggtggaggcggttcaggcggaggtggcagcggcggt
ggcgggtcgacggacatccagatgacccagtctccatcctccctgtctgc
atctgtaggagacagagtcaccatcacttgccgggcaagtcagagcatta
gcagctatttaaattggtatcagcagaaaccagggaaagcccctaagctc
ctgatctatgcggcatcccgtttgcaaagtggggtcccatcaaggttcag
tggcagtggatctgggacagatttcactctcaccatcagcagtctgcaac -continued

```
ctgaagattttgcaacttactactgtcaacagtcgcaggggaggcctgtg

acgttcggccaagggaccaaggtggaaatcaaacgggcggccgca
```

NUsc1 Protein Sequence (No His Tag)

SEQ ID NO: 4

```
MKYLLPTAAAGLLLLAAQPAMAEVQLLESGGGLVQPGGSLRLSCAASGFT

FSSYAMSWVRQAPGKGLEWVSAISNGGVETAYADSVKGRFTISRDNSKNT

LYLQMNSLRAEDTAVYYCAKNTGSFMDYWGQGTLVTVSSGGGGSGGGGSG

GGGSTDIQMTQSPSSLSASVGDRVTITCRASQSISSYLNWYQQKPGKAPK

LLIYAASRLQSGVPSRFSGSGSGTDFTLTISSLQPEDFATYYCQQSQGRP

VTFGQGTKVEIKRAAA
```

NUsc1 Heavy Chain CDR1

SEQ ID NO: 5

GFTFSSYAMS

NUsc1 Heavy Chain CDR2

SEQ ID NO: 6

AISNGGVETAYADSVKG

NUsc1 Heavy Chain CDR3

SEQ ID NO: 7

NTGSFXDY (X is any)

NUsc1 Light Chain CDR1

SEQ ID NO: 8

RASQSISSYLN

NUsc1 Light Chain CDR2

SEQ ID NO: 9

AASRLQS

NUsc1 Light Chain CDR3

SEQ ID NO: 10

QQSQGRPVT

NUsc1 Heavy Chain

SEQ ID NO: 11

```
MKYLLPTAAAGLLLLAAQPAMAEVQLLESGGGLVQPGGSLRLSCAASGFT

FSSYAMSWVRQAPGKGLEWVSAISNGGVETAYADSVKGRFTISRDNSKNT

LYLQMNSLRAEDTAVYYCAKNTGSFDYWGQGTLVTV
```

NUsc1 Light Chain

SEQ ID NO: 12

```
TDIQMTQSPSSLSASVGDRVTITCRASQSISSYLNWYQQKPGKAPKLLIY

AASRLQSGVPSRFSGSGSGTDFTLTISSLQPEDFATYYCQQSQGRPVTFG

QGTKVEIKRAAA
```

REFERENCES

The following references, some of which are cited above by number, are herein incorporated by references in their entireties.

1. S. T. Ferreira and W. L. Klein, "The Aβ oligomer hypothesis for synapse failure and memory loss in Alzheimer's disease," Neurobiology of Learning and Memory, vol. 96, no. 4. pp. 529-543, November-2011.
2. L. Mucke and D. J. Selkoe, "Neurotoxicity of amyloid β-protein: Synaptic and network dysfunction," Cold Spring Harb. Perspect. Med., vol. 2, no. 7, p. a006338, July 2012.
3. D. J. Selkoe and J. Hardy, "The amyloid hypothesis of Alzheimer's disease at 25 years," EMBO Mol. Med., vol. 8, no. 6, pp. 595-608, June 2016.
4. A. Sebollela et al., "A human scFv antibody that targets and neutralizes high molecular weight pathogenic amyloid-β oligomers," J. Neurochem., vol. 142, no. 6, pp. 934-947, July 2017.
5. World Health Organisation, "WHO|Dementia," WHO, 2017.
6. J. Cummings et al., "Alzheimer's disease drug development pipeline: 2017," Alzheimer's and Dementia: Translational Research and Clinical Interventions, vol. 3, no.
3. pp. 367-384,
7. Y. Gong et al., "Alzheimer's disease-affected brain: Presence of oligomeric A□ligands (ADDLs) suggests a molecular basis for reversible memory loss," Proc. Natl. Acad. Sci., vol. 100, no. 18, pp. 10417-10422, September 2003.
8. E. Y. Hayden and D. B. Teplow, "Amyloid β-protein oligomers and Alzheimer's disease." Alzheimers Res Ther. 2013 Nov. 29; 5(6):60.
9. T. Tomiyama et al., "A mouse model of amyloid beta oligomers: their contribution to synaptic alteration, abnormal tau phosphorylation, glial activation, and neuronal loss in vivo." J Neurosci. 2010 Apr. 7; 30(14): 4845-56.
10. M. A. Chabrier et al., "Synergistic effects of amyloid-beta and wild-type human tau on dendritic spine loss in a floxed double transgenic model of Alzheimer's disease." Neurobiol Dis. 2014 April;64:107-17.
11. D. G. Georganopoulou et al., "Nanoparticle-based detection in cerebral spinal fluid of a soluble pathogenic biomarker for Alzheimer's disease." Proc Natl Acad Sci USA. 2005 Feb. 15; 102(7):2273-6.
12. H. Fukumoto et al., "High-molecular-weight β-amyloid oligomers are elevated in cerebrospinal fluid of Alzheimer patients," FASEB J., vol. 24, no. 8, pp. 2716-2726, August 2010.
13. M. E. Larson and S. E. Lesnd. "Soluble Aβ oligomer production and toxicity." J Neurochem. 2012 January; 120 Suppl 1:125-39.
14. C. H. van Dyck, "Anti-Amyloid-β Monoclonal Antibodies for Alzheimer's Disease:," Biol. Psychiatry, vol. 83, no. 4, pp. 311-319, February 2017.
15. P. T. Velasco et al., "Synapse-binding subpopulations of Aβ oligomers sensitive to peptide assembly blockers and scFv antibodies," ACS Chem. Neurosci., vol. 3, no. 11, pp. 972-981, November 2012.
16. J. A. R. Nicolll, D. Wilkinson, C. Holmes, P. Steart, H. Markham, and R. O. Weller, "Neuropathology of human Alzheimer disease after immunization with amyloid-O peptide: A case report," Nat. Med., vol. 9, no. 4, pp. 448-452, April 2003.
17. J.-M. Orgogozo et al., "Subacute meningoencephalitis in a subset of patients with A D after A 42 immunization," Neurology, vol. 61, no. 1, pp. 46-54, July 2003.
18. I. Ferrer, M. B. Rovira, M. L. S. Guerra, M. J. Rey, and F. Costa-Jussi, "Neuropathology and Pathogenesis of Encephalitis following Amyloid R Immunization in Alzheimer's Disease," Brain Pathol., vol. 14, no. 1, pp. 11-20, January 2004.
19. J. Fuller, J. Stavenhagen, and J. L. Teeling, "New Roles for Fc receptors in neurodegeneration-The impact on Immunotherapy for Alzheimer's Disease," Front.

Neurosci., vol. 8, no. 8 JUL, p. 235, August 2014.

20. P. Holliger and P. J. Hudson, "Engineered antibody fragments and the rise of single domains," Nat Biotechnol. Sep. 23, 2005(9):1126-36.
21. P. P. Monnier et al., "In Vivo Applications of Single Chain Fv (Variable Domain) (scFv) Fragments," Antibodies 2013, 2(2), 193-208;

22. L. Huang et al., "Single-Chain Fragment Variable Passive Immunotherapies for Neurodegenerative Diseases," Int J Mol Sci. 2013 Sep.; 14(9): 19109-19127.
23. C. E. Dunbar, K. A. High, J. K. Joung, D. B. Kohn, K. Ozawa, and M. Sadelain, "Gene therapy comes of age," Science, vol. 359, no. 6372. p. eaan4672, 12 Jan. 2018.
24. M. S. Raffi et al., "A phasel study of stereotactic gene delivery of AAV2-NGF for Alzheimer's disease," Alzheimers Dement. Sep. 10, 2014 (5):571-81.
25. M. S. Raffi et al., "Adeno-Associated Viral Vector (Serotype 2)-Nerve Growth Factor for Patients With Alzheimer Disease: A Randomized Clinical Trial," JAMA Neurol. 2018 July 1; 75(7):834-841.
26. S. Jurgensen et al., "Activation of D1/D5 dopamine receptors protects neurons from synapse dysfunction induced by amyloid-β oligomers," J. Biol. Chem., vol. 286, no. 5, pp. 3270-3276, February 2011.
27. M. V. Lourenco et al., "Exercise-linked FNDC5/irisin rescues synaptic plasticity and memory defects in Alzheimer's models," Nat Med. Jan.25, 2019(1):165-175.
28. C. P. Figueiredo et al., "Memantine Rescues Transient Cognitive Impairment Caused by High-Molecular-Weight A Oligomers But Not the Persistent Impairment Induced by Low-Molecular-Weight Oligomers," J. Neurosci., vol. 33, no. 23, pp. 9626-9634, June 2013.
29. J. H. Ledo et al., "Amyloid-β oligomers link depressive-like behavior and cognitive deficits in mice," Mol Psychiatry. Oct.18, 2013(10):1053-4.
30. R. Pattali et al., "AAV9 Vector: a Novel modality in gene therapy for spinal muscular atrophy," Gene Ther. August26, 2019(7-8):287-295.
31. E. Hurdy and L. H. Vandenberghe, "Therapeutic AAV Gene Transfer to the Nervous System: A Clinical Reality," Neuron. 2019 Mar. 6; 101(5):839-862.
32. M. Piton et al., "Alzheimer's Disease: Advances in Drug Development," J Alzheimers Dis. 2018; 65(1):3-13.
33. J. Sevigny et al., "The antibody aducanumab reduces Aβ plaques in Alzheimer's disease." Nature. 2016 Sep. 1; 537(7618):50-6.
34. D. Cuchet et al., "Characterization of antiproliferative and cytotoxic properties of the HSV-1 immediate-early ICP0 protein." J Gene Med. Sep.7, 2005 (9):1187-99.
35. M. P. Lambert et al., "Diffusible, nonfibrillar ligands derived from Abetal-42 are potent central nervous system neurotoxins." Proc Natl Acad Sci USA. 1998 May 26;95(11):6448-53.
36. B. A. Chromy et al., "Self-assembly of Abeta(1-42) into globular neurotoxins." Biochemistry. 2003 Nov. 11; 42(44):12749-60.
37. A. Sebollela et al., "Amyloid-β oligomers induce differential gene expression in adult human brain slices." J Biol Chem. 2012 Mar. 2; 287(10):7436-45.
38. F. G. de Felice et al., "Abeta oligomers induce neuronal oxidative stress through an N-methyl-D-aspartate receptor-dependent mechanism that is blocked by the Alzheimer drug memantine." J Biol Chem. 2007 Apr. 13; 282(15):11590-601.
39. F. G. de Felice et al., "Protection of synapses against Alzheimer's-linked toxins: insulin signaling prevents the pathogenic binding of Abeta oligomers." Proc Natl Acad Sci US A. 2009 Feb. 10; 106(6):1971-6.
40. M. P. Lambert et al., "Monoclonal antibodies that target pathological assemblies of Abeta." J Neurochem. 2007 January;100(1):23-35.
41. D. Puzzo et al., "Amyloid-beta peptide inhibits activation of the nitric oxide/cGMP/cAMP-responsive element-binding protein pathway during hippocampal synaptic plasticity." J Neurosci. 2005 July 20; 25(29): 6887-97.
42. K. J. Livak and T. D. Schmittgen, "Analysis of relative gene expression data using real-time quantitative PCR and the 2(-Delta Delta C(T)) Method." Methods. Dec.25, 2001 (4):402-8.

The invention claimed is:

1. A composition comprising an antibody or antibody fragment comprising an antigen-binding region comprising (a) a heavy chain variable region comprising a complementarity determining region 1 (CDR) amino acid sequence of SEQ ID NO: 5, a CDR2 amino acid sequence of SEQ ID NO: 6, and a CDR3 amino acid sequence of SEQ ID NO: 7, and (b) a light chain variable region comprising a CDR1 amino acid sequence of SEQ ID NO: 8, a CDR2 amino acid sequence of SEQ ID NO: 9, and a CDR3 amino acid sequence of SEQ ID NO: 10.

2. The composition of claim 1, wherein the antibody or antibody fragment is a single-chain variable fragment (ScFv).

3. The composition of claim 2, wherein the ScFv comprises at least 70% sequence identity with SEQ ID NO: 4.

4. The composition of claim 1, wherein the polynucleotide comprises 70% sequence identity with SEQ ID NO: 3.

* * * * *

SEQUENCE LISTING

```
Sequence total quantity: 22
SEQ ID NO: 1            moltype = DNA  length = 814
FEATURE                 Location/Qualifiers
source                  1..814
                        mol_type = other DNA
                        organism = Synthetic construct
SEQUENCE: 1
atgaaatacc tattgcctac ggcagccgct ggattgttat tactcgcggc ccagccggcc  60
atggccgagg tgcagctgtt ggagtctggg ggaggcttgg tacagcctgg ggggtccctg  120
agactctcct gtgcagcctc tggattcacc tttagcagct atgccatgag ctgggtccgc  180
caggctccag ggaaggggct ggagtgggtc tcagcgattt cgaatggggg tgtggagaca  240
gcgtacgcag actccgtgaa gggccggttc accatctcca gagacaattc caagaacacg  300
ctgtatctgc aaatgaacag cctgagagcc gaggacacgg ccgtatatta ctgtgcgaaa  360
aatactggtt cgtttgacta ctggggccag ggaaccctgg tcaccgtctc gagcggtgga  420
ggcggttcag gcggaggtgg cagcggcggt ggcgggtcga cggacatcca gatgacccag  480
tctccatcct ccctgtctgc atctgtagga gacagagtca ccatcacttg ccgggcaagt  540
cagagcatta gcagctattt aaattggtat cagcagaaac cagggaaagc ccctaagctc  600
ctgatctatg cggcatcccg tttgcaaagt ggggtcccat caaggttcag tggcagtgga  660
tctgggacag atttcactct caccatcagc agtctgcaac ctgaagattt tgcaacttac  720
tactgtcaac agtcgcaggg gaggcctgtg acgttcggcc aagggaccaa ggtggaaatc  780
aaacgggcgg ccgcacatca tcatcaccat cacg                              814

SEQ ID NO: 2            moltype = AA  length = 271
FEATURE                 Location/Qualifiers
source                  1..271
                        mol_type = protein
                        organism = Synthetic construct
SEQUENCE: 2
MKYLLPTAAA GLLLLAAQPA MAEVQLLESG GGLVQPGGSL RLSCAASGFT FSSYAMSWVR  60
QAPGKGLEWV SAISNGGVET AYADSVKGRF TISRDNSKNT LYLQMNSLRA EDTAVYYCAK  120
```

```
NTGSFDYWGQ GTLVTVSSGG GGSGGGGSGG GGSTDIQMTQ SPSSLSASVG DRVTITCRAS  180
QSISSYLNWY QQKPGKAPKL LIYAASRLQS GVPSRFSGSG SGTDFTLTIS SLQPEDFATY  240
YCQQSQGRPV TFGQGTKVEI KRAAAHHHHH H                                 271

SEQ ID NO: 3             moltype = DNA  length = 795
FEATURE                  Location/Qualifiers
source                   1..795
                         mol_type = other DNA
                         organism = Synthetic construct
SEQUENCE: 3
atgaaatacc tattgcctac ggcagccgct ggattgttat tactcgcggc ccagccggcc  60
atggccgagg tgcagctgtt ggagtctggg ggaggcttgg tacagcctgg ggggtccctg  120
agactctcct gtgcagcctc tggattcacc tttagcagct atgccatgag ctgggtccgc  180
caggctccag ggaaggggct ggagtgggtc tcagcgattt cgaatggggg tgtggagaca  240
gcgtacgcag actccgtgaa gggccggttc accatctcca gagacaattc caagaacacg  300
ctgtatctgc aaatgaacag cctgagagcc gaggacacgg ccgtatatta ctgtgcgaaa  360
aatactggtt cgtttgacta ctggggccag ggaaccctgg tcaccgtctc gagcggtgga  420
ggcggttcag gcggaggtgg cagcggcggt ggcgggtcga cggacatcca gatgacccag  480
tctccatcct ccctgtctgc atctgtagga gacagagtca ccatcacttg ccgggcaagt  540
cagagcatta gcagctattt aaattggtat cagcagaaac cagggaaagc ccctaagctc  600
ctgatctatg cggcatcccg tttgcaaagt ggggtcccat caaggttcag tggcagtgga  660
tctgggacag atttcactct caccatcagc agtctgcaac ctgaagattt tgcaacttac  720
tactgtcaac agtcgcaggg gaggcctgtg acgttcggcc aagggaccaa ggtggaaatc  780
aaacgggcgg ccgca                                                    795

SEQ ID NO: 4             moltype = AA  length = 265
FEATURE                  Location/Qualifiers
source                   1..265
                         mol_type = protein
                         organism = Synthetic construct
SEQUENCE: 4
MKYLLPTAAA GLLLLAAQPA MAEVQLLESG GGLVQPGGSL RLSCAASGFT FSSYAMSWVR  60
QAPGKGLEWV SAISNGGVET AYADSVKGRF TISRDNSKNT LYLQMNSLRA EDTAVYYCAK  120
NTGSFDYWGQ GTLVTVSSGG GGSGGGGSGG GGSTDIQMTQ SPSSLSASVG DRVTITCRAS  180
QSISSYLNWY QQKPGKAPKL LIYAASRLQS GVPSRFSGSG SGTDFTLTIS SLQPEDFATY  240
YCQQSQGRPV TFGQGTKVEI KRAAA                                         265

SEQ ID NO: 5             moltype = AA  length = 10
FEATURE                  Location/Qualifiers
source                   1..10
                         mol_type = protein
                         organism = Synthetic construct
SEQUENCE: 5
GFTFSSYAMS                                                          10

SEQ ID NO: 6             moltype = AA  length = 17
FEATURE                  Location/Qualifiers
source                   1..17
                         mol_type = protein
                         organism = Synthetic construct
SEQUENCE: 6
AISNGGVETA YADSVKG                                                  17

SEQ ID NO: 7             moltype = AA  length = 8
FEATURE                  Location/Qualifiers
source                   1..8
                         mol_type = protein
                         organism = Synthetic construct
SEQUENCE: 7
NTGSFXDY                                                            8

SEQ ID NO: 8             moltype = AA  length = 11
FEATURE                  Location/Qualifiers
source                   1..11
                         mol_type = protein
                         organism = Synthetic construct
SEQUENCE: 8
RASQSISSYL N                                                        11

SEQ ID NO: 9             moltype = AA  length = 7
FEATURE                  Location/Qualifiers
source                   1..7
                         mol_type = protein
                         organism = Synthetic construct
SEQUENCE: 9
AASRLQS                                                             7

SEQ ID NO: 10            moltype = AA  length = 9
FEATURE                  Location/Qualifiers
```

-continued

```
source                  1..9
                        mol_type = protein
                        organism = Synthetic construct
SEQUENCE: 10
QQSQGRPVT                                                         9

SEQ ID NO: 11           moltype = AA  length = 136
FEATURE                 Location/Qualifiers
source                  1..136
                        mol_type = protein
                        organism = Synthetic construct
SEQUENCE: 11
MKYLLPTAAA GLLLLAAQPA MAEVQLLESG GGLVQPGGSL RLSCAASGFT FSSYAMSWVR  60
QAPGKGLEWV SAISNGGVET AYADSVKGRF TISRDNSKNT LYLQMNSLRA EDTAVYYCAK  120
NTGSFDYWGQ GTLVTV                                                 136

SEQ ID NO: 12           moltype = AA  length = 112
FEATURE                 Location/Qualifiers
source                  1..112
                        mol_type = protein
                        organism = Synthetic construct
SEQUENCE: 12
TDIQMTQSPS SLSASVGDRV TITCRASQSI SSYLNWYQQK PGKAPKLLIY AASRLQSGVP  60
SRFSGSGSGT DFTLTISSLQ PEDFATYYCQ QSQGRPVTFG QGTKVEIKRA AA         112

SEQ ID NO: 13           moltype = DNA  length = 18
FEATURE                 Location/Qualifiers
source                  1..18
                        mol_type = other DNA
                        organism = Synthetic construct
SEQUENCE: 13
tattactcgc ggcccagc                                               18

SEQ ID NO: 14           moltype = DNA  length = 18
FEATURE                 Location/Qualifiers
source                  1..18
                        mol_type = other DNA
                        organism = Synthetic construct
SEQUENCE: 14
ctatgcggcc ccattcag                                               18

SEQ ID NO: 15           moltype = DNA  length = 24
FEATURE                 Location/Qualifiers
source                  1..24
                        mol_type = other DNA
                        organism = Synthetic construct
SEQUENCE: 15
gctagctatt actcgcggcc cagc                                        24

SEQ ID NO: 16           moltype = DNA  length = 24
FEATURE                 Location/Qualifiers
source                  1..24
                        mol_type = other DNA
                        organism = Synthetic construct
SEQUENCE: 16
tcgcgactat gcggccccat tcag                                        24

SEQ ID NO: 17           moltype = DNA  length = 20
FEATURE                 Location/Qualifiers
source                  1..20
                        mol_type = other DNA
                        organism = Synthetic construct
SEQUENCE: 17
tcagcagaaa ccagggaaag                                             20

SEQ ID NO: 18           moltype = DNA  length = 21
FEATURE                 Location/Qualifiers
source                  1..21
                        mol_type = other DNA
                        organism = Synthetic construct
SEQUENCE: 18
ctgctgatgg tgagagtgaa a                                           21

SEQ ID NO: 19           moltype = DNA  length = 21
FEATURE                 Location/Qualifiers
source                  1..21
                        mol_type = other DNA
                        organism = Synthetic construct
SEQUENCE: 19
```

-continued

```
tgtgacgttg acatccgtaa a                                          21

SEQ ID NO: 20          moltype = DNA  length = 20
FEATURE                Location/Qualifiers
source                 1..20
                       mol_type = other DNA
                       organism = Synthetic construct
SEQUENCE: 20
gtacttgcgc tcaggaggag                                            20

SEQ ID NO: 21          moltype = DNA  length = 20
FEATURE                Location/Qualifiers
source                 1..20
                       mol_type = other DNA
                       organism = Synthetic construct
SEQUENCE: 21
atccctgaaa agttccagca                                            20

SEQ ID NO: 22          moltype = DNA  length = 20
FEATURE                Location/Qualifiers
source                 1..20
                       mol_type = other DNA
                       organism = Synthetic construct
SEQUENCE: 22
ccctcttggt gaggtcaatg                                            20
```